United States Patent
Miyazaki et al.

(10) Patent No.: US 8,470,162 B2
(45) Date of Patent: *Jun. 25, 2013

(54) BIOSENSOR, THIN FILM ELECTRODE FORMING METHOD, QUANTIFICATION APPARATUS, AND QUANTIFICATION METHOD

(75) Inventors: Shoji Miyazaki, Ehime (JP); Masaki Fujiwara, Ehime (JP); Yoshinobu Tokuno, Ehime (JP)

(73) Assignee: Panasonic Corporation, Osaka (JP)

( * ) Notice: Subject to any disclaimer, the term of this patent is extended or adjusted under 35 U.S.C. 154(b) by 88 days.

This patent is subject to a terminal disclaimer.

(21) Appl. No.: 12/930,957

(22) Filed: Jan. 20, 2011

(65) Prior Publication Data

US 2011/0147234 A1 Jun. 23, 2011

Related U.S. Application Data

(63) Continuation of application No. 10/809,217, filed on Mar. 25, 2004, now Pat. No. 7,998,325, which is a continuation of application No. 09/889,243, filed as application No. PCT/JP00/08012 on Nov. 14, 2000, now Pat. No. 6,875,327.

(30) Foreign Application Priority Data

| Nov. 15, 1999 | (JP) | 11-324551 |
|---|---|---|
| Apr. 12, 2000 | (JP) | 2000-111255 |
| Apr. 14, 2000 | (JP) | 2000-113754 |
| Apr. 25, 2000 | (JP) | 2000-124394 |
| Apr. 27, 2000 | (JP) | 2000-128249 |
| Apr. 28, 2000 | (JP) | 2000-130158 |

(51) Int. Cl.
*G01N 27/327* (2006.01)

(52) U.S. Cl.
USPC .................. 205/777.5; 205/792; 205/775

(58) Field of Classification Search
USPC .............. 204/403.01–403.15; 205/777.5, 205/778, 792, 775
See application file for complete search history.

(56) References Cited

U.S. PATENT DOCUMENTS

| 4,225,410 A | 9/1980 | Pace |
| 4,310,614 A | 1/1982 | Connell et al. |

(Continued)

FOREIGN PATENT DOCUMENTS

| CN | 1057131 A | 12/1991 |
| CN | 1057492 A | 1/1992 |

(Continued)

OTHER PUBLICATIONS

USPTO Office Action dated Jan. 20, 2011 in connection with U.S. Appl. No. 12/322,684.

(Continued)

*Primary Examiner* — Alex Noguerola
(74) *Attorney, Agent, or Firm* — Amster, Rothstein & Ebenstein LLP

(57) ABSTRACT

Quantifying devices and methods are disclosed for quantifying substrate content using a biosensor where the methods include a first detecting step for detecting an electrical change generated between a measuring electrode and a counter electrode of a biosensor by applying a sample liquid to the biosensor; a second detecting step for detecting an electrical change generated between a detecting electrode of the biosensor and the counter electrode or the measuring electrode by applying the sample liquid to the biosensor; and a notification step for informing a user when the second detecting step does not occur within a predetermined period after the first detecting step.

5 Claims, 24 Drawing Sheets

U.S. PATENT DOCUMENTS

| | | | |
|---|---|---|---|
| 4,337,279 A | 6/1982 | Polak | |
| 4,426,451 A | 1/1984 | Columbus | |
| 4,444,848 A | 4/1984 | Shanefield et al. | |
| 4,465,576 A | 8/1984 | Negishi et al. | |
| 4,683,048 A | 7/1987 | Yamada et al. | |
| 4,938,860 A | 7/1990 | Wogoman | |
| 5,002,811 A | 3/1991 | Bauer et al. | |
| 5,100,526 A | 3/1992 | Ito | |
| 5,120,420 B1 | 6/1992 | Nankai et al. | |
| 5,171,689 A | 12/1992 | Kawaguri et al. | |
| 5,230,866 A | 7/1993 | Shartle et al. | |
| 5,264,103 A | 11/1993 | Yoshioka et al. | |
| 5,266,179 A | 11/1993 | Nankai et al. | |
| 5,288,636 A | 2/1994 | Pollmann et al. | |
| 5,302,846 A | 4/1994 | Matsumoto | |
| 5,324,414 A | 6/1994 | Spahn et al. | |
| 5,352,351 A | 10/1994 | White et al. | |
| 5,384,028 A | 1/1995 | Ito | |
| 5,407,867 A | 4/1995 | Iwasaki et al. | |
| 5,437,999 A | 8/1995 | Diebold et al. | |
| 5,487,810 A | 1/1996 | Thurm et al. | |
| 5,512,159 A | 4/1996 | Yoshioka et al. | |
| 5,565,085 A | 10/1996 | Ikeda et al. | |
| 5,582,697 A | 12/1996 | Ikeda et al. | |
| 5,650,062 A | 7/1997 | Ikeda et al. | |
| 5,651,869 A | 7/1997 | Yoshioka et al. | |
| 5,672,256 A | 9/1997 | Yee | |
| 5,683,400 A | 11/1997 | McGuire | |
| 5,759,364 A | 6/1998 | Charlton et al. | |
| 5,762,770 A | 6/1998 | Pritchard et al. | |
| 5,795,774 A | 8/1998 | Matsumoto et al. | |
| 5,863,400 A | 1/1999 | Drummond et al. | |
| 5,912,134 A | 6/1999 | Shartle | |
| 5,942,102 A | 8/1999 | Hodges et al. | |
| 5,985,116 A | 11/1999 | Ikeda et al. | |
| 5,989,409 A | 11/1999 | Kurnik et al. | |
| 6,004,441 A | 12/1999 | Fujiwara et al. | |
| 6,071,391 A | 6/2000 | Gotoh et al. | |
| 6,120,676 A | 9/2000 | Heller et al. | |
| 6,132,683 A | 10/2000 | Sugihara et al. | |
| 6,143,164 A | 11/2000 | Heller et al. | |
| 6,156,270 A | 12/2000 | Buechler | |
| 6,179,979 B1 | 1/2001 | Hodges et al. | |
| 6,258,229 B1 | 7/2001 | Winarta et al. | |
| 6,287,451 B1 | 9/2001 | Winarta et al. | |
| 6,299,757 B1 * | 10/2001 | Feldman et al. | 205/775 |
| 6,309,526 B1 | 10/2001 | Fujiwara et al. | |
| 6,338,790 B1 | 1/2002 | Feldman et al. | |
| 6,416,641 B1 | 7/2002 | Ikeda et al. | |
| 6,475,372 B1 | 11/2002 | Ohara et al. | |
| 6,531,040 B2 | 3/2003 | Musho et al. | |
| 6,576,101 B1 | 6/2003 | Heller et al. | |
| 6,576,117 B1 | 6/2003 | Iketaki et al. | |
| 6,592,745 B1 | 7/2003 | Feldman et al. | |
| 6,599,406 B1 | 7/2003 | Kawanaka et al. | |
| 6,632,349 B1 | 10/2003 | Hodges et al. | |
| 6,645,359 B1 | 11/2003 | Bhullar et al. | |
| 6,662,439 B1 | 12/2003 | Bhullar | |
| 6,716,577 B1 | 4/2004 | Yu et al. | |
| 6,841,052 B2 | 1/2005 | Musho et al. | |
| 6,875,321 B2 | 4/2005 | Ding et al. | |
| 6,875,327 B1 * | 4/2005 | Miyazaki et al. | 204/403.14 |
| 6,923,894 B2 | 8/2005 | Huang et al. | |
| 7,018,843 B2 | 3/2006 | Heller | |
| 7,041,210 B2 | 5/2006 | Hodges et al. | |
| 7,050,843 B2 | 5/2006 | Shartle et al. | |
| 7,073,246 B2 | 7/2006 | Bhullar et al. | |
| 7,250,105 B1 | 7/2007 | Davies et al. | |
| 7,258,769 B2 | 8/2007 | Cui et al. | |
| 7,276,146 B2 | 10/2007 | Wilsey | |
| 7,276,147 B2 | 10/2007 | Wilsey | |
| 7,287,318 B2 | 10/2007 | Bhullar et al. | |
| 7,338,639 B2 | 3/2008 | Burke et al. | |
| 7,386,937 B2 | 6/2008 | Bhullar et al. | |
| 7,998,325 B2 | 8/2011 | Miyazaki et al. | |
| 8,025,780 B2 | 9/2011 | Miyazaki et al. | |
| 8,142,629 B2 | 3/2012 | Miyazaki et al. | |
| 8,287,703 B2 | 10/2012 | Bhullar et al. | |
| 8,349,157 B2 | 1/2013 | Miyazaki et al. | |
| 2004/0178066 A1 | 9/2004 | Miyazaki et al. | |
| 2004/0178067 A1 | 9/2004 | Miyazaki et al. | |
| 2009/0056120 A1 | 3/2009 | Bhullar et al. | |
| 2009/0152111 A1 | 6/2009 | Miyazaki et al. | |
| 2010/0012517 A1 | 1/2010 | Feldman et al. | |
| 2010/0112517 A1 | 5/2010 | Chen | |
| 2011/0117269 A1 | 5/2011 | Miyazaki et al. | |
| 2011/0174613 A1 | 7/2011 | Miyazaki et al. | |
| 2011/0272296 A1 | 11/2011 | Miyazaki et al. | |
| 2011/0278167 A1 | 11/2011 | Miyazaki et al. | |

FOREIGN PATENT DOCUMENTS

| | | |
|---|---|---|
| EP | 0311377 A2 | 12/1989 |
| EP | 0311377 A3 | 12/1989 |
| EP | 0 471 986 A | 2/1992 |
| EP | 0573101 A1 | 12/1993 |
| EP | 0460918 B1 | 9/1995 |
| EP | 0 732 406 | 9/1996 |
| GB | 2 224 356 A | 5/1990 |
| JP | 60-7191 | 1/1985 |
| JP | 1-291153 | 11/1989 |
| JP | 2-1535 | 1/1990 |
| JP | 2-128153 | 5/1990 |
| JP | 3-75552 | 3/1991 |
| JP | 4-132949 | 5/1992 |
| JP | 5-72172 | 3/1993 |
| JP | 5-505459 | 8/1993 |
| JP | 6-109688 | 4/1994 |
| JP | 6-58338 | 8/1994 |
| JP | 7-209242 | 8/1995 |
| JP | 8-320304 | 12/1996 |
| JP | 9159644 | 6/1997 |
| JP | 9-189675 | 7/1997 |
| JP | 10-170471 | 6/1998 |
| JP | 10311817 | 11/1998 |
| JP | 11-94791 | 4/1999 |
| JP | H11-108879 | 4/1999 |
| JP | Hei11/1999-94790 | 4/1999 |
| JP | Hei11/1999-201933 | 7/1999 |
| JP | 11-248667 | 9/1999 |
| JP | 2000-121594 | 4/2000 |
| WO | WO 91/09139 | 6/1991 |
| WO | WO 97/02487 | 1/1997 |
| WO | WO 99/05516 | 2/1999 |
| WO | WO 00/20626 | 4/2000 |
| WO | 0125775 A1 | 4/2001 |
| WO | 2004113900 A2 | 12/2004 |

OTHER PUBLICATIONS

USPTO Office Action dated Aug. 23, 2012 in connection with U.S. Appl. No. 13/490,553.

USPTO Office Action dated Aug. 30, 2012 in connection with U.S. Appl. No. 12/930,627.

USPTO Office Action dated Sep. 14, 2012 in connection with U.S. Appl. No. 13/930,919.

USPTO Notice of Allowance and Fee(s) Due dated Sep. 24, 2010 in connection with U.S. Appl. No. 12/322,684, filed Feb. 5, 2009.

USPTO Office Action dated Nov. 23, 2010 in connection with U.S. Appl. No. 12/802,573, filed Jun. 9, 2010.

European Search Report received by European Patent office dated Jun. 29, 2010 in connection with European Patent Application No. 09177290, 6 pages.

USPTO Notice of Allowance and Fee(s) Due dated Jun. 22, 2010 in connection with U.S. Appl. No. 12/322,684, filed Feb. 5, 2009.

USPTO Notice of Allowance and Fee(s) Due dated Feb. 19, 2010 in connection with U.S. Appl. No. 12/322,684, filed Feb. 5, 2009.

USTPO Office Action dated Sep. 16, 2009 in connection with U.S. Appl. No. 12/322,684, filed Feb. 5, 2009.

USPTO Office Action dated May 5, 2009 in connection with U.S. Appl. No. 10/809,240, filed Mar. 25, 2004.

Communication From European Patent Office dated Apr. 23, 2009 in connection with European Patent Application No. 00974977.1, 5 pages.

USPTO Office Action dated Oct. 17, 2008 in connection with U.S. Appl. No. 10/809,240, filed Mar. 25, 2004.

USPTO Office Action dated Oct. 3, 2012 in connection with U.S. Appl. No. 13/135,848.

USPTO Office Action dated Oct. 4, 2012 in connection with U.S. Appl. No. 13/135,816.

USPTO Notice of Allowance and Fee(s) Due dated Nov. 26, 2012 in connection with U.S. Appl. No. 13/490,553.

Wilson Gs et al., "Unmediated Amperometric Enzyme Electrodes," in Biosensors: A Practical Approach, pp. 1-17 (A.E.G. Cass ed., 1990).

Tender et al., "Electrochemical Patterning of Self-Assembled Monolayers Onto Microscopic Arrays of Gold Electrodes Fabricated by Laser Ablation," Langmuir, vol. 12 (1996), at pp. 5515-5518.

Bergveld et al., "Fabrication and Mass Production," in Advances in Biosensors: A Research Annual—Chemical Sensors for in Vivo Monitoring 165, 165-186 (Turner ed., Supp. 1, 1993).

Kreider et al., "Sputtered Thin-Film pH Electrodes of Platinum, Palladium, Ruthenium, and Iridium Oxides," Sensors & Actuators B, vol. 28 (1995), pp. 167-172.

Mizutani et al., "Amperometric Biosensors Using an Enzyme-Containing Polyion Complex," in Polymers in Sensors 46-56 (Akmal et al. ed., 1998).

Matsumoto et al., "A Micro-Planar Amperometric Glucose Sensor Unsusceptible to Interference Species," Sensors & Actuators B, vol. 49 (1998), pp. 68-72.

Van Gerwen et al., "Nanoscaled Interdigitated Electrode Arrays for Biochemical Sensors," Sensors & Actuators B, vol. 49 (1998), pp. 73-80.

Steinschaden et al., "Miniaturised Thin Film Conductometric Biosensors With High Dynamic Range and High Sensitivity," Sensors & Actuators B, vol. 44 (1997), pp. 365-369.

Sohn et al., "ISFET Glucose and Sucrose Sensors by Using Platinum Electrode and Photo-Crosslinkable Polymers," Sensors & Actuators B, vol. 41 (1997), at pp. 7-11.

Zhou et al., "A Miniaturized Glucose biosensor Based on the Coimmobilization of Glucose Oxidase and Ferrocene Perchlorate in Nafion at a Microdisk Platinum Electrode," Sensors & Actuators B, vol. 40 (1997), at pp. 89-94.

Sheppard et al., "Microfabricated Conductimetric pH Sensor," Sensors & Actuators B, vol. 28 (1995), at pp. 95-102.

Paeschke et al., "Highly Sensitive Electrochemical Microsensors Using Submicrometer Electrode Arrays," Sensors & Actuators B, vol. 26-27 (1995), at pp. 394-97.

Schalkhammer et al., "Microfabricated Glucose, Lactate, Glutamate and Glutamine Thin-Film Biosensors," Sensors & Actuators B, vol. 18-19 (1994), at pp. 587-591.

Kasapbasioglu et al., "An Impedance Based Ultra-Thin Platinum Island Film Glucose Sensor," Sensors & Actuators B, vol. 13-14 (1993), at pp. 749-751.

Sheppard et al., "Electrical Conductivity Measurements Using Microfabricated Interdigitated Electrodes," Anal. Chem., vol. 85 (1993), at pp. 1199-1202.

Karube et al., "Trends in Biosensor Research and Development," Sensors & Actuators B, vol. 13-14 (1993), at pp. 12-15.

Morris et al., "An Electrochemical Capillary Fill Device for the Analysis of Glucose Incorporating Glucose Oxidase and Ruthenium (III) Hexamine as Mediator," Electroanalysis, vol. 4 (1992), at pp. 1-9.

Nishizawa et al., "Penicillin Sensor Based on a Microarray Electrode Coated with pH-Responsive Polypyrrole," Analytical Chemistry, vol. 64 (1992), at pp. 2642-2644.

Gregg et al., "Cross-Linked Redox Gels Containing Glucose Oxidase for Amperometric Biosensor Applications," Analytical Chemistry, vol. 62 (1990), at pp. 258-263.

Malitesta et al., "Glucose Fast-Response Amperometric Sensor Based on Glucose Oxidase Immobilized in an Electropolymerized Poly (o-phenylenediamine) Film," Analytical Chemistry, vol. 62 (1990), at pp. 2735-2740.

Preidel et al., "In Vitro Measurements with Electrocatalytic Glucose Sensor in Blood," Biomed. Biochem. Acta, vol. 48 (1989), at pp. 897-903.

Taylor et al., "An Acetylcholine Receptor-Based Biosensor for the Detection of Cholinergic Agents," Analytica Chimica Acta, vol. 213 (1988), at pp. 131-138.

Williams et al., "Electrochemical-Enzymatic Analysis of Blood Glucose and Lactate," Analytical Chemistry, vol. 42 (1970), at pp. 118-121.

Vaivars et al., "Influence of Thin Film Coatings on the Gas Sensitivity Properties of Narrow Laser Cut Gap in In2O3 on Glass Substrate," Sensors & Actuators B, vol. 33 (1996), at pp. 173-77.

Kleperis et al., "Gas-Sensitive Gap Formation by Laser Ablation in In2O3 Layer: Application as Humidity Sensor," Sensors & Actuators B, vol. 28 (1995), at pp. 135-38.

Meier Dj et al., "Laser Structuring of Fine Lines," Circuitree, vol. 13 (2000), pp. 36-42.

Tahhan I, "Biocompatible Microstructuring of Polymers and Electrodes with an Excimer Laser," MEDICS Workshop 2000 Speakers Abstracts.

Qin et al., "Excimer Laser Patterning on Thin Polymer Surfaces for Electrochemical Gas Sensors," Proceedings of the International Conference on Lasers (1999).

* cited by examiner

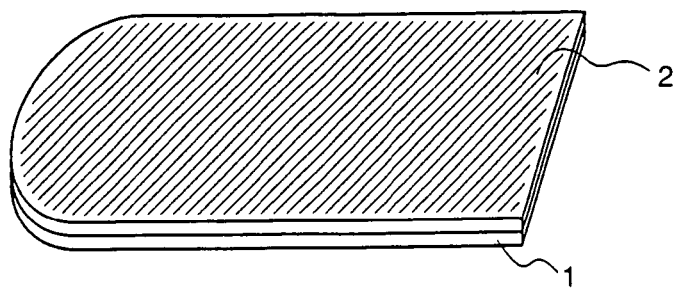
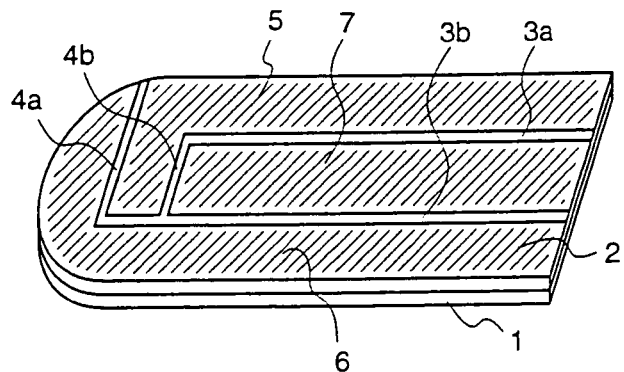
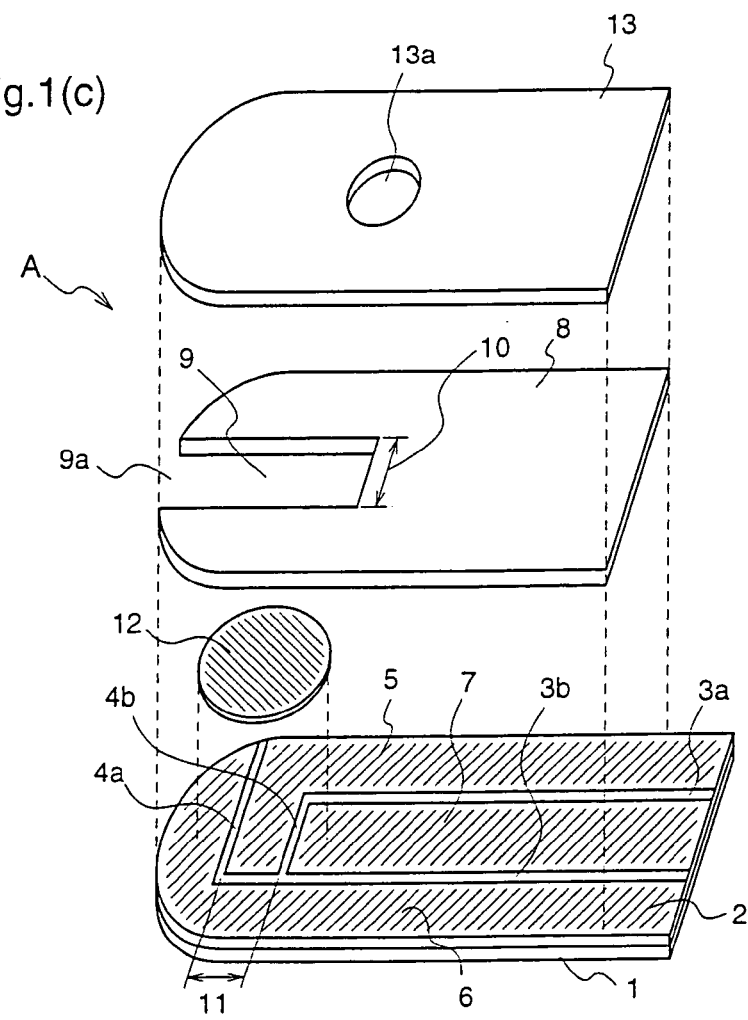

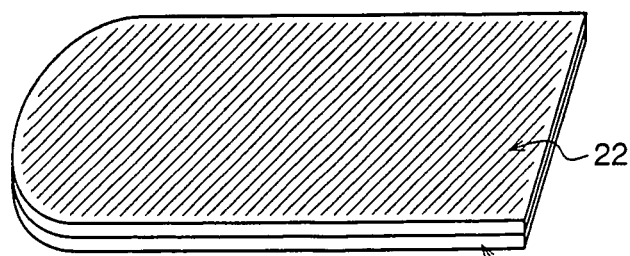
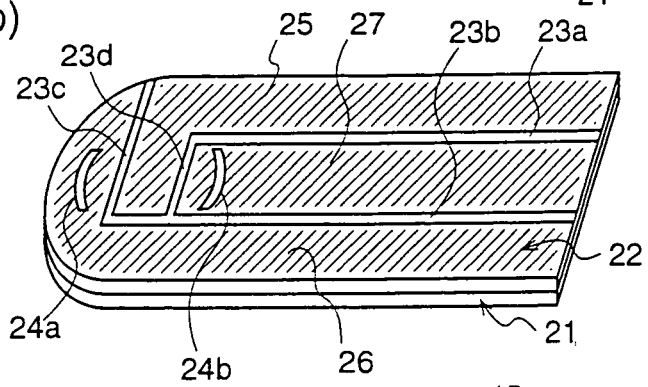
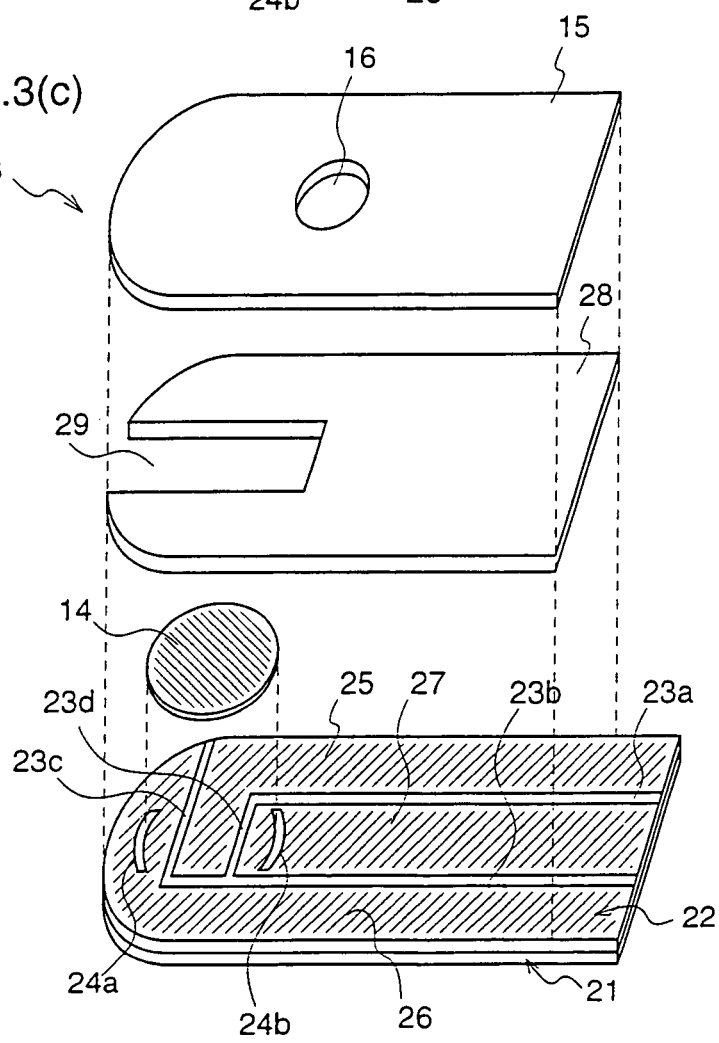

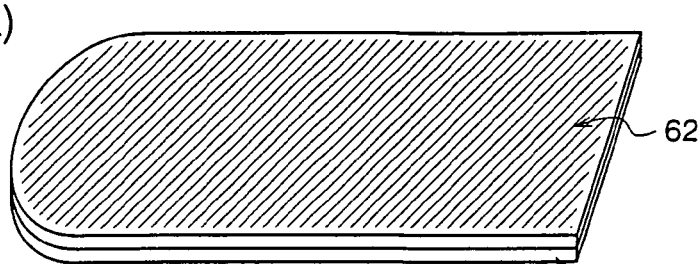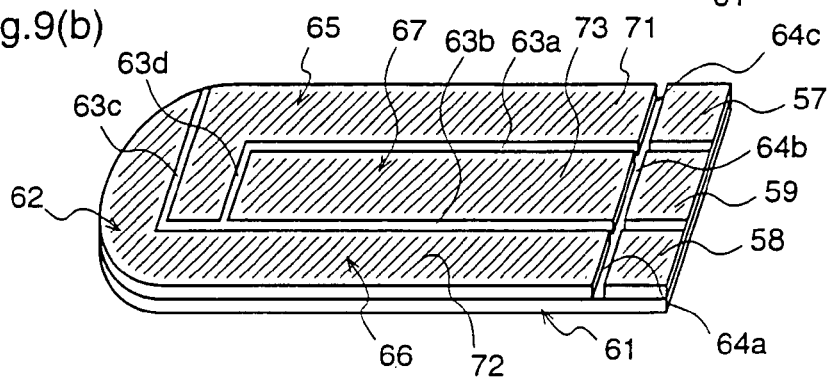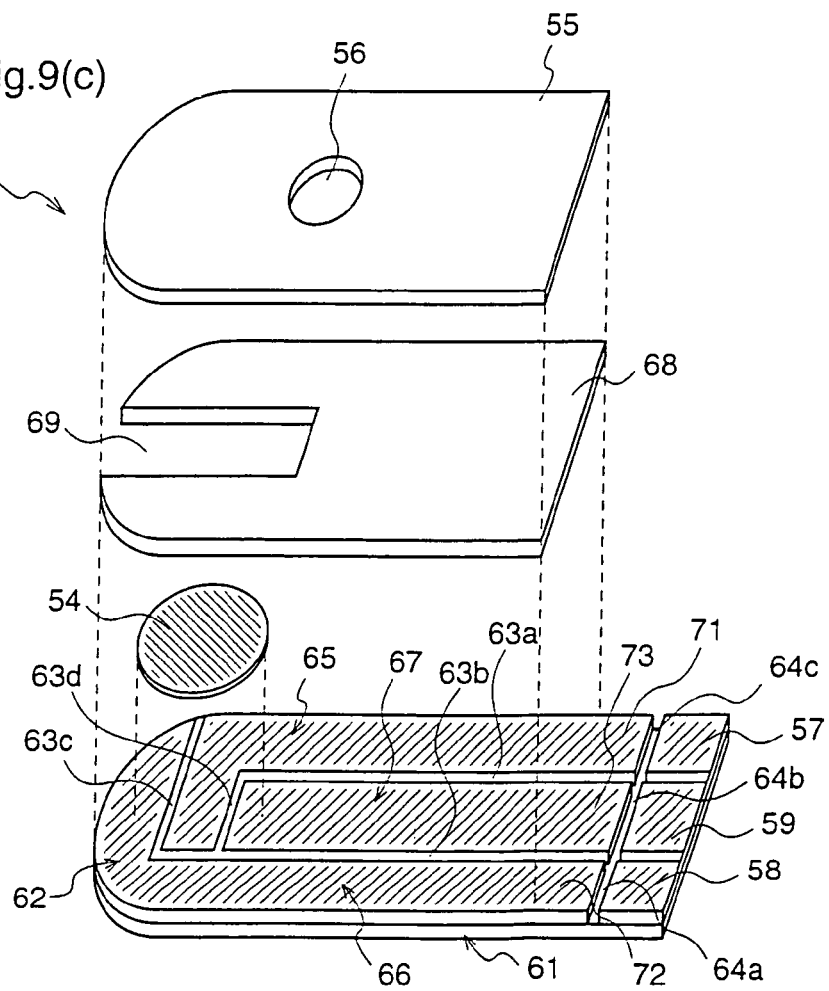

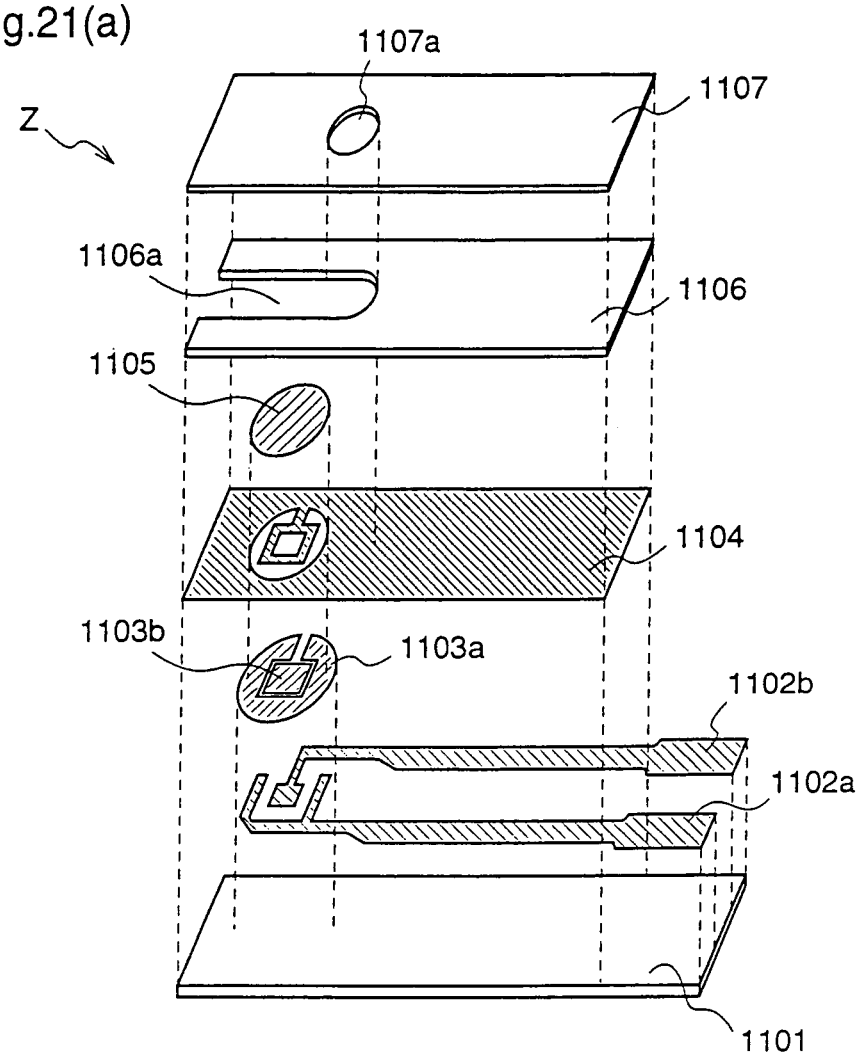
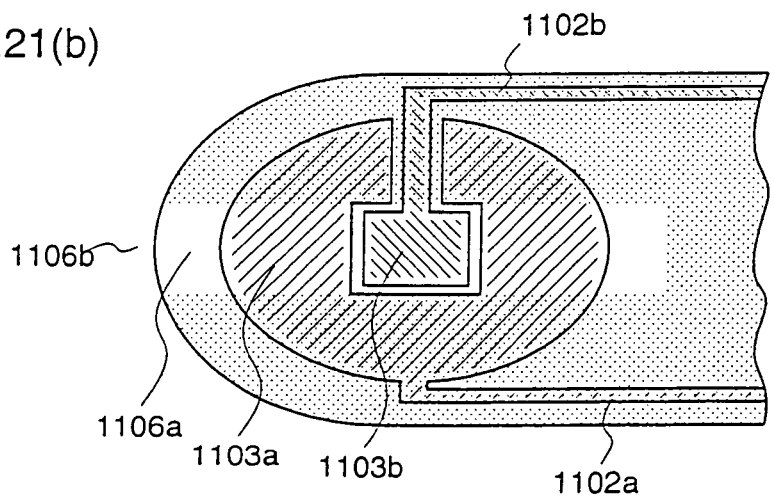

BIOSENSOR, THIN FILM ELECTRODE FORMING METHOD, QUANTIFICATION APPARATUS, AND QUANTIFICATION METHOD

CROSS-REFERENCE TO RELATED APPLICATIONS

This application is a continuation of U.S. patent application Ser. No. 10/809,217, filed Mar. 25, 2004, now U.S. Pat. No. 7,998,325, which is a continuation of U.S. patent application Ser. No. 09/889,243, filed Oct. 1, 2001, now U.S. Pat. No. 6,875,327, which is a national stage entry under 35 U.S.C. §371 of PCT International Patent Application No. PCT/JP00/08012, filed Nov. 14, 2000, which claims priority of Japanese Patent Application No. 11/324,551, filed Nov. 15, 1999, Japanese Patent Application No. 2000/111255, filed Apr. 12, 2000, Japanese Patent Application No. 2000/113754, filed Apr. 14, 2000, Japanese Patent Application No. 2000/124394, filed Apr. 25, 2000, Japanese Patent Application No. 2000/128249, filed Apr. 27, 2000, and Japanese Patent Application No. 2000/130158, filed Apr. 28, 2000, the contents of all of which are hereby incorporated by reference into the subject application.

TECHNICAL FIELD

The present invention relates to a biosensor which quantifies a substrate included in a sample liquid, a thin film electrode forming method suitable at the manufacture of this biosensor, as well as a quantification apparatus and a quantification method using the biosensor and, more particularly, to a biosensor which provides a low manufacture error and a stable performance, a thin film electrode forming method used in manufacturing electrodes of the biosensor, as well as a quantification apparatus and a quantification method using the biosensor.

BACKGROUND ART

A biosensor is a sensor which utilizes a molecule recognizing capacity of a biological material such as microorganisms, enzymes, antibodies, DNA, and RNA and applies a biological material as a molecular discrimination element to quantify a substrate included in a sample liquid. That is, the substrate included in the sample liquid is quantified by utilizing a reaction which is caused when a biological material recognizes an objective substrate, such as an oxygen consumption due to respiration of a microorganism, an enzyme reaction, and a luminous reaction. Among various biosensors, an enzyme sensor has progressively come into practical use, and an enzyme sensor as a biosensor for, for example, glucose, lactic acid, cholesterol, and amino acid is utilized in the medical diagnostics or food industry. This enzyme sensor reduces an electron transfer agent by an electron which is generated by a reaction of a substrate included in a sample liquid as a specimen and enzyme or the like, and a quantification apparatus electrochemically measures a reduction quantity of the transfer agent, thereby performing quantitative analysis of the specimen.

Various models of such biosensor are proposed.

Hereinafter, a biosensor Z as a conventional biosensor will be described.

FIG. 21(a) is an exploded perspective view of a biosensor Z and FIG. 21(b) is a diagram illustrating a I structure of an electrode part formed at the tip of the biosensor Z.

The biosensor Z has its respective members which are bonded in positional relationships shown by dotted lines in FIG. 21(a).

The electrode part of the biosensor Z is formed through three printing processes as described below.

In the first process, a silver paste with a high electrical conductivity is printed on an insulating support 1101 by a screen printing method and dried to form electrode lead parts 1102a and 1102b.

In the second process, a carbon paste is printed on the electrode lead parts 1102a and 1102b and dried to form a counter electrode 1103a and a working electrode 1103b. The working electrode 1103b is located inside the ring-shaped counter electrode 1103a, and the counter electrode 1103a and the working electrode 1103b is in contact with the electrode lead parts 1102a and 1102b, respectively.

In the third process, a insulating paste 1104 as an insulating material is printed on the counter electrode 1103a and the working electrode 1103b and dried to define areas of the counter electrode 1103a and the working electrode 1103b.

A reagent including enzyme or the like is applied to the counter electrode 1103a and the working electrode 1103b which are formed on the support 1101 as described above, whereby a reagent layer 1105 is formed, and a spacer 1106 having a cutout part 1106a for forming a specimen supply path and a cover 1107 having an air hole 1107a are further laminated thereon and bonded. One end of the cutout part 1106a of the spacer 1106 leads to the air hole 1107a provided in the cover 1107. As shown in FIG. 21(b), the arrangements of the counter electrode 1103a and the working electrode 1103b which are formed on the support 1101 are such that the counter electrode 1103a is located at a position nearest to an inlet 1106b of the specimen supply path and the working electrode 1103b and the counter electrode 1103a are located in the inner part thereof.

A description will be given of a method for quantifying a substrate in a sample liquid in the so-constructed biosensor Z with reference to FIG. 21(b).

The sample liquid (hereinafter, also referred to as "specimen") is supplied to the inlet 1106b of the specimen supply path in a state where a fixed voltage is applied between the counter electrode 1103a and the working electrode 1103b by a quantification apparatus (hereinafter, also referred to as "measuring device") connected to the biosensor Z. The specimen is drawn inside the specimen supply path by capillary phenomenon, passes on the counter electrode 1103a nearer to the inlet 1106b, and reaches to the working electrode 1103a, and a dissolution of the reagent layer 1105 is started. At this point of time, the quantification apparatus detects an electrical change occurring between the counter electrode 1103a and the working electrode 1103b, and starts a quantification operation. In this way, the substrate included in the sample liquid is quantified.

Since this biosensor Z has variations in output characteristics for each production lot, it is required to correct variations in the output characteristics in a measuring device for practical use. A conventional method for coping this will be described below.

FIG. 22 is a diagram illustrating a state where the biosensor Z is inserted in a measuring device. Numeral 4115 denotes a measuring device in which the biosensor Z is inserted. Numeral 4116 denotes an opening of the measuring device 4115, into which the biosensor Z is inserted. Numeral 4117 denotes a display part of the measuring device 4115 for displaying a measuring result.

The measuring device 4115 has correction data according to the output characteristics for each production lot, and subjects an output of the biosensor Z to the correction which is required for each production lot to obtain a correct blood sugar level. Therefore, it is required to insert a correction chip (not shown here) which is specified for each production lot into the insertion opening 4116 of the measuring device 4115 before the measurement, thereby designating the required correction data to the measuring device 4115. The correction chip has information about the correction data to be used, and is inserted in the insertion opening 4116, whereby the measuring device 4115 prepares the required correction data. The correction chip is taken out from the insertion opening 4116, the biosensor Z is inserted in the opening 4116 of the measuring device 4115, and then the substrate included in a specimen is quantified as described above. The measuring device 4115 to which a correction value is inputted as described above obtains a correct blood sugar level from a measured current value and correction data, and displays the blood sugar level at the display part 4117.

The above-described conventional biosensor Z has problems to be solved.

First, in the biosensor Z, a silver paste, a carbon paste or the like is printed on the support by the screen printing method and laminated to define the area of the working electrode. Accordingly, the area of the working electrode varies with blurs or sags of various pastes at the printing process, and it is difficult to make the uniform area of the working electrode. In addition, since the electrode structure is composed of three layers, i.e., Ag, carbon, and insulating paste, it is very complicated and requires an advanced printing technique. Further, since the electrode part of the biosensor Z consists of two electrodes, i.e., the working electrode and the counter electrode, when a quantification apparatus connected to the biosensor Z applies a certain voltage between these two electrodes and an electrical change occurs, it detects that the specimen has reached the working electrode and starts measuring. However, it starts the measurement also when an immeasurably slight amount of specimen covers the working electrode. Thus, an incorrect display in the measured value occurs due to the shortage of the specimen quantity. In the biosensor Z, it is required to enhance wettability between a reaction reagent layer and a carbon electrode and improve their adhesion to increase sensor sensitivity. For that purpose, a polishing processing or heat processing to the electrode surface is conventionally performed after the carbon electrode is formed. However, this increases man-day, resulting in an increase in costs, or variations in polishing processing accuracy causes variations in the sensor accuracy. Further, the carbon paste used for the screen printing is generally a composite material which is composed of binder resin, graphite, carbon black, organic solvent and the like, and the paste characteristics are easily changed due to lots of respective raw materials, manufacturing conditions in paste kneading or the like. Therefore, it is required a strict control for mass manufacture of stable sensors, resulting in considerable troubles.

Further, only by applying the reagent on electrodes for the reagent layer formation, the reagent cannot uniformly be applied on the electrodes because of the surface state of the electrode of a difference in the way in which the reagent spreads due to reagent liquid composition, whereby variations in the reagent quantity on the electrodes occur. That is, even when the same amount of reagent is applied by dripping, variations in spread of the reagent occur, resulting in variations in position or area of the reagent layer. Therefore, the performance of the biosensor Z is deteriorated.

Further, it is considerably troublesome to insert the correction chip for every measurement, and when it is forgotten to insert the correction chip, a correction chip for example for measuring lactic acid value is inserted by mistake, or a correction chip which is for measuring blood sugar level but has different output characteristics is inserted, there occurs an error in a measured result.

The present invention is made to solve the above-mentioned problems, and has for its object to provide a biosensor which can be formed by a simple manufacturing method and has a high measuring accuracy, a biosensor in which a reagent layer is disposed uniformly on electrodes regardless of a reagent liquid composition, resulting in an uniform performance, a biosensor which enables a measuring device to discriminate correction data for each production lot only by being inserted therein without a correction chip being inserted, a thin film electrode forming method for these biosensors, as well as a method and an apparatus for quantifying using the biosensors.

DISCLOSURE OF THE INVENTION

According to the present invention, there is provided a biosensor for quantifying a substrate included in a sample liquid comprising: a first insulating support and a second insulating support; an electrode part comprising at least a working electrode and a counter electrode; a specimen supply path for introducing the sample liquid to the electrode part; and a reagent layer employed for quantifying the substrate included in the sample liquid, and the electrode part, the specimen supply path, and the reagent layer exist between the first insulating support and the second insulating support, the specimen supply path is provided on the electrode part, and the reagent layer is provided on the electrode part in the specimen supply path, respectively, and the electrode part is dividedly formed by first slits provided on an electrical conductive layer which is formed on the whole or part of an internal surface of one or both of the first insulating support and the second insulating support.

Since a biosensor is constructed as described above, an electrode part can be defined easily and with a high accuracy, and variations in response of each biosensor can be reduced, resulting in a favorable response. Further, the electrode part is formed in a monolayer of electrical conductive layer, whereby troubles can be reduced and an electrode part with a smooth surface can be formed by a simple method. Since the structure of the electrode part is quite simple, it is possible to easily form biosensors having the same performance.

According to an embodiment of the present invention, in the biosensor, the electrode part further comprises a detecting electrode.

Since the biosensor is constructed as described above, it is possible to make the biosensor have a better accuracy.

According to an embodiment of the present invention, in the biosensor, the counter electrode is provided on the whole or part of the internal surface of the second insulating support, the working electrode and the detecting electrode are provided on the whole or part of the internal surface of the first insulating support, and the working electrode and the detecting electrode which are provided on the internal surface of the first insulating support are dividedly formed by the first slits provided on the electrical conductive layer.

Since the biosensor is constructed as described above, it is possible to downscale a specimen supply path, whereby a measurement can be done with a slight amount of specimen.

According to an embodiment of the present invention, in the biosensor, the electrode part is provided on the whole or part of the internal surface of only the first insulating support, and the electrode part provided on the internal surface of the first insulating support is dividedly formed by the first slits provided on the electrical conductive layer.

Since the biosensor is constructed as described above, all of the electrodes are provided on the same surface, and thus the electrodes are formed only on one surface, resulting in an easier manufacture, whereby the manufacturing costs of the biosensor can be reduced.

According to an embodiment of the present invention, in the biosensor, an area of the counter electrode is equal to or larger than that of the working electrode.

Since the biosensor is constructed as described above, an electron transfer reaction between the counter electrode and the working electrode is prevented to be rate-determined, thereby promoting the reaction smoothly.

According to an embodiment of the present invention, in the biosensor, a total of an area of the counter electrode and an area of the detecting electrode is equal to or larger that that of the working electrode.

Since the biosensor is constructed as described above, electron transfer reactions between the counter electrode as well as the detecting electrode and the working electrode are prevented to be rate-determined, thereby promoting the reactions smoothly.

According to an embodiment of the present invention, in the biosensor, the area of the detecting electrode in the specimen supply path of the biosensor is equal to the area of the counter electrode.

Since the biosensor is constructed as described above, electron transfer reactions between the counter electrode as well as the detecting electrode and the working electrode are more reliably prevented to be rate-determined, thereby promoting the reactions smoothly.

According to an embodiment of the present invention, in the biosensor, a spacer is provided which has a cutout part for forming the specimen supply path and is placed on the electrode part, and the second insulating support is placed on the spacer.

Since the biosensor is constructed as described above, the position where the specimen supply path is provided is fixed, and the second insulating support is placed thereon, thereby preventing the specimen introduced to the specimen supply path from leaking from the specimen supply path.

According to an embodiment of the present invention, in the biosensor, the spacer and the second insulating support is integral.

Since the biosensor is constructed as described above, the spacer and the second insulating support is integral, thereby to enable a cost reduction and a simple manufacture.

According to an embodiment of the present invention, in the biosensor, an air hole leading to the specimen supply path is formed.

Since the biosensor is constructed as described above, excessive air is discharged from the air hole when the specimen is introduced to the specimen supply path, thereby reliably introducing the specimen to the specimen supply path due to the capillary phenomenon.

According to an embodiment of the present invention, in the biosensor, the reagent layer is formed by dripping a reagent, and second slits are provided around a position where the reagent is dripped.

Since the biosensor is constructed as described above, when the reagent is dripped on the electrodes for the reagent layer formation, thereby forming the reagent layer, the reagent spreads uniformly forming the reagent layer of a prescribed area at the prescribed position, whereby the reagent layer free from variations in the position and area can be formed, resulting in a correct measurement free from the variations.

According to an embodiment of the present invention, in the biosensor, the second slits are arc shaped.

Since the biosensor is constructed as described above, the spread of the reagent is defined by the slits which have the same shapes as that of the reagent spread, thereby defining the area and the position of the reagent layer more correctly.

According to an embodiment of the present invention, in the biosensor, third slits are provided for dividing the electrical conductive layer to define an area of the electrode part.

Since the biosensor is constructed as described above, when the support is initially cut at the manufacturing process of the biosensor, the area of each electrode is previously defined by the third slits, whereby the area of each electrode does not change due to the cut position of the support, thereby preventing variations in the accuracy.

According to an embodiment of the present invention, in the biosensor, shapes of the first insulating support and the second insulating support are approximately rectangular, and one third slit or two or more third slits are provided in parallel with one side of the approximate rectangle shape.

Since the biosensor is constructed as described above, the area of each electrode can be defined easily by the third slits, and the area of each electrode does not change due to deviations of the cut position when the support is cut, resulting in no variation in the accuracy.

According to an embodiment of the present invention, the biosensor has information of correction data generated for each production lot of the biosensor, which correspond to characteristics concerning output of an electrical change resulting from a reaction between the reagent liquid and the reagent layer and can be discriminated by a measuring device employing the biosensor.

Since the biosensor is constructed as described above, the measuring device can discriminate which the correction data is required, only by inserting the biosensor into the measuring device, and there is no need for a user to input the information about the correction data employing a correction chip or the like, thereby removing troubles and preventing operational errors to obtain a correct result.

According to an embodiment of the present invention, in the biosensor, one or plural fourth slits dividing the electrode part are provided, and the measuring device can discriminate the information of the correction data according to positions of the fourth slits.

Since the biosensor is constructed as described above, the measuring device can discriminate the information of the correction data by the positions of the fourth slits, the correction data can be indicated correspondingly to plural production lots, the measuring device can easily discriminate which correction data is required, by inserting the biosensor into the measuring device, whereby there is no operational trouble, resulting in preventing operational errors to obtain a correct result.

According to an embodiment of the present invention, in the biosensor, at least one or all of the first slits, the second slits, the third slits, and the fourth slits are formed by processing the electrical conductive layer by a laser.

Since the biosensor is constructed as described above, a high-accuracy processing is possible, the area of each electrode can be defined with a high accuracy, and further the clearance between the respective electrodes can be narrowed, resulting in a small-size biosensor.

According to an embodiment of the present invention, in the biosensor, a slit width of respective one of the first slits, the second slits, the third slits, and the fourth slits is 0.005 mm to 0.3 mm.

Since the biosensor is constructed as described above, the clearance between the respective electrodes can be narrowed, resulting in a small-size biosensor.

According to an embodiment of the present invention, in the biosensor, a slit depth of respective one of the first slits, the second slits, the third slits, and the fourth slits is equal to or larger than the thickness of the electrical conductive layer.

Since the biosensor is constructed as described above, there can be obtained a biosensor in which the respective electrodes are surely separated.

According to an embodiment of the present invention, in the biosensor, the reagent layer includes an enzyme.

Since the biosensor is constructed as described above, there can be obtained an enzyme biosensor suitable for an inspection which employs the enzyme.

According to an embodiment of the present invention, in the biosensor, the reagent layer includes an electron transfer agent.

Since the biosensor is constructed as described above, there can be obtained a biosensor suitable for an inspection utilizing a reaction of the electron transfer agent.

According to an embodiment of the present invention, in the biosensor, the reagent layer includes a hydrophilic polymer.

Since the biosensor is constructed as described above, there can be obtained a high-accuracy biosensor which can easily form the reagent layer.

According to an embodiment of the present invention, in the biosensor, the insulating support is made of a resin material.

Since the biosensor is constructed as described above, it is possible to manufacture a lower-cost biosensor.

According to an embodiment of the present invention, there is provided a thin film electrode forming method for forming a thin film electrode on a surface of an insulating support including: a roughened surface forming step of roughening the surface of the insulating support by colliding an excited gas against the surface of the insulating support in a vacuum atmosphere; and an electrical conductive layer forming step of forming the electrical conductive layer as a thin film electrode which is composed of a conductive substance on the roughened surface of the insulating support.

Since the thin film electrode is formed as described above, a preprocessing such as a surface polishing processing is not required, whereby it is possible to form the thin film electrode by a simpler method and to form the thin film electrode with high adhesion between the support and the electrode layer.

According to an embodiment of the present invention, in the thin film electrode forming method, the roughed surface forming step comprises: a support placing step of placing the insulating support in a vacuum chamber; an evacuation step of evacuating the vacuum chamber; a gas filling step of filling up the vacuum chamber with a gas; and a colliding step of exciting the gas to be ionized and colliding the same against the insulating support.

Since the thin film electrode is formed as described above, it is possible to form the support surface suitable for forming the thin film electrode more effectively and reliably, thereby forming the thin film electrode more effectively.

According to an embodiment of the present invention, in the thin film electrode forming method, a degree of the vacuum in the evacuation step is within a range of $1 \times 10^{-1}$ to $3 \times 10^{-3}$ pascals.

Since the thin film electrode is formed as described above, it is possible to form the support surface suitable for forming the thin film electrode more reliably, thereby forming the thin film electrode more effectively.

According to an embodiment of the present invention, in the thin film electrode forming method, the gas is an inert gas.

Since the thin film electrode is formed as described above, the support surface can be made in a state suitable for forming the thin film electrode without denaturing the support surface.

According to an embodiment of the present invention, in the thin film electrode forming method, the inert gas is either a rare gas of argon, neon, helium, krypton, and xenon, or nitrogen.

Since the thin film electrode is formed as described above, there can be formed the thin film electrode more reliably without denaturing the support surface.

According to an embodiment of the present invention, in the thin film electrode forming method, the electrical conductive layer forming step comprises: a second support placing step of placing an insulating support having an already roughened surface, which has been subjected to the roughened surface forming step, in a second vacuum chamber; a second evacuation step of evacuating the second vacuum chamber; a second gas filling step of filling up the second vacuum chamber with a second gas; and a step of exciting the second gas to be ionized and colliding the same against a conductive substance to beat out atoms of the conductive substances, to form a film on the insulating support having the already roughened surface.

Since the thin film electrode is formed as described above, a preprocessing such as a surface polishing processing is not required and the thin film electrode with higher adhesion to the support can be obtained.

According to an embodiment of the present invention, in the thin film electrode forming method, the electrical conductive layer forming step comprises: a second support placing step of placing an insulating support having an already roughened surface, which has been subjected to the roughened surface forming step, in a second vacuum chamber; a second evacuation step of evacuating the second vacuum chamber; and a step of heating and evaporating a conductive substance to deposit steams as a film on the insulating support having the already roughened surface.

Since the thin film electrode is formed as described above, a preprocessing such as a surface polishing processing is not required and the thin film electrode with higher adhesion to the support can be obtained.

According to an embodiment of the present invention, in the thin film electrode forming method, a degree of the vacuum in the second evacuation step is within a range of $1 \times 10^{-1}$ to $3 \times 10^{-3}$ pascals.

Since the thin film electrode is formed as described above, there can be more reliably formed the thin film electrode with remarkably high adhesion to the support.

According to an embodiment of the present invention, in the thin film electrode forming method, the second gas is an inert gas.

Since the thin film electrode is formed as described above, there can be formed the thin film electrode with high adhesion to the support without denaturing the support surface and the thin film electrode itself.

According to an embodiment of the present invention, in the thin film electrode forming method, the inert gas is either a rare gas of argon, neon, helium, krypton and xenon, or nitrogen.

Since the thin film electrode is formed as described above, there can be more reliably formed the thin film electrode with high adhesion to the support without denaturing the support surface and the thin film electrode itself.

According to an embodiment of the present invention, in the thin film electrode forming method, the vacuum chamber and the second vacuum chamber is the same chamber.

Since the thin film electrode is formed as described above, a facility for forming the thin film electrode can be simplified and thus the manufacturing cost of the thin film electrode can be reduced.

According to an embodiment of the present invention, in the thin film electrode forming method, the conductive substance is a noble metal or carbon.

Since the thin film electrode is formed as described above, the thin film electrode is composed of not a composite material but a single substance material, thereby enabling a mass manufacture of stable electrodes, which is not influenced by the manufacturing conditions and which has a less difference in material lots.

According to an embodiment of the present invention, in the thin film electrode forming method, a thickness of a formed thin film electrode is within a range of 3 nm to 100 nm.

Since the thin film electrode is formed as described above, the thickness of the electrode can be thinned as much as possible, thereby to enhance a production tact as well as reduce a manufacturing cost due to a reduction of the material cost.

According to an embodiment of the present invention, in the biosensor, the electrical conductive layer is formed by the thin film electrode forming method.

Since the biosensor is formed as described above, the thin film electrode reflects unevenness on the support surface which is processed into a roughened surface, so that the wettability and adhesiveness between the electrode and the reagent is enhanced, resulting in a high performance biosensor.

According to an embodiment of the present invention, there is provided a quantification method for quantifying, by employing the biosensor, a substrate included in a sample liquid supplied to the biosensor comprising: a first application step of applying a voltage between the detecting electrode and the counter electrode or the working electrode; a reagent supplying step of supplying the sample liquid to the reagent layer; a first change detecting step of detecting an electrical change occurring between the detecting electrode and the counter electrode or the working electrode by the supply of the sample liquid to the reagent layer; a second application step of applying a voltage between the working electrode and the counter electrode as well as the detecting electrode after the electrical change is detected in the first change step; and a current measuring step of measuring a current generated between the working electrode and the counter electrode as well as the detecting electrode, to which the voltage is applied in the second application step.

Since the quantification is performed as described above, the quantification operation is started when the electrical change occurs between the detecting electrode and the working electrode or the counter electrode of the biosensor, thereby preventing measuring errors due to the shortage of the specimen amount supplied to the reagent layer, resulting in a higher accuracy measurement. Further, when the measurable amount of specimen is supplied to the reagent layer, the measurement is performed by using the detecting electrode also as the counter electrode, thereby making the area of the electrode part smaller, and thus a quantitative analysis based on a slight amount of specimen can be performed correctly.

According to an embodiment of the present invention, there is provided a quantification method for quantifying, by employing the biosensor, a substrate included in a sample liquid supplied to the biosensor comprising: a third application step of applying a voltage between the detecting electrode and the counter electrode or the working electrode as well as between the working electrode and the counter electrode; a reagent supplying step of supplying the sample liquid to the reagent layer; a first change detecting step of detecting an electrical change occurring between the detecting electrode and the counter electrode or the working electrode by the supply of the sample liquid to the reagent layer; a second change detecting step of detecting an electrical change occurring between the working electrode and the counter electrode by the supply of the sample liquid to the reagent layer; a second application step of applying a voltage between the working electrode and the counter electrode as well as the detecting electrode after the electrical changes are detected in the first change detecting step and the second change detecting step; and a current measuring step of measuring a current generated between the working electrode and the counter electrode as well as the detecting electrode, to which the voltage is applied in the second application step.

Since the quantification is performed as described above, the quantification operation is started when the electrical change occurs between the detecting electrode and the working electrode or the counter electrode of the biosensor, thereby preventing measuring errors due to the shortage of the specimen amount supplied to the reagent layer, resulting in a higher accuracy measurement. Further, when the measurable amount of specimen is supplied to the reagent layer, the measurement is performed by using the detecting electrode also as the counter electrode, thereby making the area of the electrode part smaller, and thus quantitative analysis based on a slight amount of specimen can be performed correctly.

According to an embodiment of the present invention, in the quantification method, the second change detecting step is followed by a no-change informing step of informing a user that no change occurs when it is detected that no electrical change occurs between the detecting electrode and the counter electrode or the working electrode for a prescribed period of time.

Since the quantification is performed as described above, it is possible to inform a user that there is a shortage of the specimen amount supplied to the reagent layer of the biosensor, resulting in the quantification method with enhanced convenience and safety.

According to an embodiment of the present invention, there is provided a quantification apparatus, to which the biosensor is detachably connected and which quantifies a substrate included in a sample liquid supplied to the biosensor comprising: a first current/voltage conversion circuit for converting a current from the working electrode included in the biosensor into a voltage; a first A/D conversion circuit for digitally converting the voltage from the current/voltage conversion circuit; a first switch provided between the counter electrode included in the biosensor and the ground; and a control part for controlling the first A/D conversion circuit and the first switch, and the control part applies a voltage between the detecting electrode and the working electrode in a state where the first switch is insulated from the counter electrode, detects an electrical change between the detecting electrode and the working electrode occurring by the sample liquid which is supplied to the reagent layer on the specimen supply path, thereafter applies a voltage between the working electrode and the counter electrode as well as the detecting electrode in a state where the first switch is connected to the counter electrode, and measures a response current generated by applying the voltage.

Since the quantification apparatus is constructed as described above, measuring errors due to the shortage of the specimen amount supplied to the reagent layer of the specimen supply path are prevented, resulting in a higher accuracy measurement. Further, the detecting electrode of the biosensor is used also as the counter electrode at the measuring, so that the specimen supply path can be downscaled, thereby to perform a quantitative analysis of a slight amount of specimen correctly.

According to an embodiment of the present invention, there is provided a quantification apparatus, to which the biosensor is detachably connected and which quantifies a substrate included in a sample liquid supplied to the biosensor comprising: a first current/voltage conversion circuit for converting a current from the working electrode included in the biosensor into a voltage; a second current/voltage conversion circuit for converting a current from the detecting electrode included in the biosensor into a voltage; a first A/D conversion circuit for digitally converting the voltage from the first current/voltage conversion circuit; a second A/D conversion circuit for digitally converting the voltage from the second current/voltage conversion circuit; a first selector switch for switching the connection of the detecting electrode of the biosensor to the first current/voltage conversion circuit or the ground; and a control part for controlling the first A/D conversion circuit, the second A/D conversion circuit, and the first selector switch, and the control part applies a voltage between the detecting electrode and the counter electrode as well as between the working electrode and the counter electrode in a state where the first selector switch is connected to the first current/voltage conversion circuit, detects an electrical change between the detecting electrode and the working electrode as well as an electrical change between the working electrode and the counter electrode, respectively, occurring by the sample liquid which is supplied to the reagent layer provided on the specimen supply path, thereafter connects the first selector switch to the ground, applies a voltage between the working electrode and the counter electrode as well as the detecting electrode, and measures a response current generated by applying the voltage.

Since the quantification apparatus is constructed as described above, measuring errors due to the shortage of the specimen amount supplied to the reagent layer of the specimen supply path are prevented, resulting in a higher accuracy measurement. Further, the detecting electrode of the biosensor is used also as the counter electrode at the measuring, so that the specimen supply path can be downscaled, thereby to perform a quantitative analysis of a slight amount of specimen correctly.

According to an embodiment of the present invention, the quantification apparatus comprises: a second selector switch for switching the connection of the working electrode of the biosensor to the second current/voltage conversion circuit or the ground, and the control part applies a voltage between the detecting electrode and the counter electrode as well as between the working electrode and the counter electrode in a state where the first selector switch is connected to the first current/voltage conversion circuit and the second selector switch is connected to the second current/voltage conversion circuit, respectively, connects the second selector switch to the ground when detecting an electrical change between the working electrode and the counter electrode, occurring by the sample liquid which is supplied to the reagent layer provided on the specimen supply path, and when thereafter detecting an electrical change between the detecting electrode and the working electrode, in a state where the second selector switch is connected to the second current/voltage conversion circuit and the first selector switch is connected to the ground, applies a voltage between the working electrode and the counter electrode as well as the detecting electrode, and measures a response current generated by applying the voltage.

Since the quantification apparatus is constructed as described above, measuring errors due to the shortage of the specimen amount supplied to the reagent layer of the specimen supply path are prevented, resulting in a higher accuracy measurement. Further, the detecting electrode of the biosensor is used also as the counter electrode at the measuring, so that the specimen supply path can be downscaled, thereby to perform a quantitative analysis of a slight amount of specimen correctly.

According to an embodiment of the present invention, the quantification apparatus comprising an informing means for informing a user that no change occurs, when the sample liquid is supplied to the reagent layer of the specimen supply path, and the control part detects that an electrical change occurs between the working electrode and the counter electrode but no electrical change occurs between the detecting electrode and the working electrode or the counter electrode.

Since the quantification apparatus is constructed as described above, it is possible to inform a user of the shortage of the specimen amount supplied to the reagent layer of the specimen supply path of the biosensor, resulting in the quantification apparatus with enhanced convenience and safety.

BRIEF DESCRIPTION OF DRAWINGS

FIG. 1 are exploded perspective views of a biosensor according to a first and a fifth embodiments.

FIG. 3 are exploded perspective views of a biosensor according to a second embodiment.

FIG. 9 are exploded perspective views of a biosensor according to a fourth embodiment.

FIGS. 21(a)-(b) are exploded perspective views of a conventional biosensor.

BEST MODE TO EXECUTE THE INVENTION

Figure 2A:
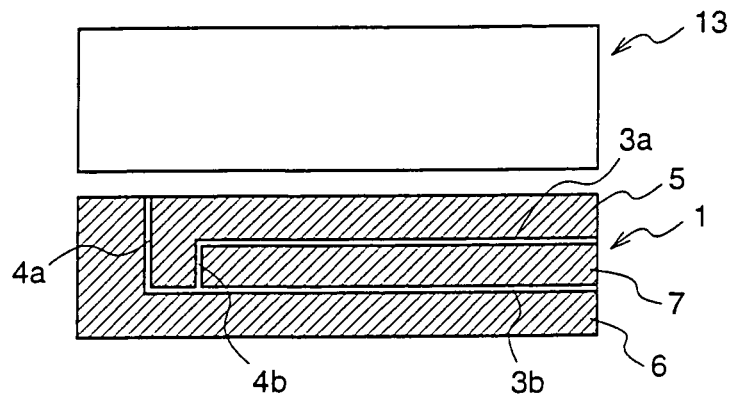
FIG. 2 are diagrams exemplifying how an electrode part is provided.

Hereinafter, embodiments of the present invention will be described with reference to the figures. The embodiments which are described here are merely examples, and the present invention is not necessarily restricted thereto.

Embodiment 1

A biosensor A as defined in the present invention will be described as a first embodiment with reference to the figures.

FIGS. 1(a) to 1(c) are exploded perspective views of the biosensor A according to the first embodiment of the present invention.

First, members constituting the biosensor A will be described.

Numeral 1 denotes a first insulating support (hereinafter, referred to as merely "support") composed of polyethylene terephthalate or the like. Numeral 2 denotes a conductive layer which is formed on the whole surface of the support 1 and composed of an electrical conductive material such as a noble metal, for example gold or palladium, and carbon. Numerals 3a and 3b denote slits which are provided on the conductive layer 2 on the support 1 and are parallel to the side of the support 1. Numerals 4a and 4b denote slits which are provided on the conductive layer 2 on the support 1 and are vertical to the side of the support 1. Numerals 5, 6, and 7 denote a working electrode, a counter electrode, and a detecting electrode, which are formed by dividing the conductive layer 2 by the slits 3a and 3b, as well as 4a and 4b. Numeral 8 denotes a spacer which covers the working electrode 5, the counter electrode 6, and the detecting electrode 7 on the support 1. Numeral 9 denotes a rectangular cutout part provided in the middle of an entering edge part of the spacer 8 to form a specimen supply path. Numeral 9a denotes an inlet of the specimen supply path, numeral 10 denotes a longitudinal width of the cutout part 9 of the spacer 8, and numeral 11 denotes an clearance between the two slits 4a and 4b which are provided on the conductive layer 2. Numeral 12 denotes a reagent layer which is formed by applying a reagent including enzyme or the like to the working electrode 5, the counter electrode 6, and the detecting electrode 7 which are exposed from the cutout part 9 of the spacer 8. Numeral 13 denotes a cover (second insulating support) for covering the spacer 8, and numeral 13a denotes an air hole provided in the middle of the cover 13.

A method for manufacturing the so-constructed biosensor A will be described with reference to figures.

First, as shown in FIG. 1(a), an electrical conductive material such as a noble metal, for example gold or palladium, and carbon is subjected to the screen printing method, a sputtering evaporating method or the like, thereby to form the conductive layer 2 on the whole surface of the support 1.

Next, as shown in FIG. 1(b), two slits 3a and 3b parallel to the side of the support 1 as well as two slits 4a and 4b vertical to the slits 3a and 3b are formed on the conductive layer 2 which is formed on the support 1 by employing a laser, to divide into the counter electrode 6, the working electrode 5, and the detecting electrode 7. At this time, the slits 4a and 4b are provided so that an interval between a tip of the support 1 and the slit 4a is equivalent to or larger than the interval 11 between the two slits 4a and 4b.

As another manufacturing method for providing the three electrodes on the support 1, it is also possible to use a printing plate, a masking plate or the like (not shown here) in which a pattern required to form the conductive layer 2 having parallel two slits 3a and 3b is previously arranged when an electrical conductive material or the like is formed on the support 1 by the screen printing method, sputtering evaporating method or the like, and thereafter use the laser to the conductive layer 2 which is formed on the support 1 to provide the slits 4a and 4b, to divide into the working electrode 5, counter electrode 6, and the detecting electrode 7, whereby it is possible to form electrode parts. Further, it is also conceivable to apply a method in which a printing plate, a masking plate or the like in which a pattern required to form the conductive layer 2 having two slits 3a and 3b parallel to the side of the support 1 and two slits 4a and 4b vertical thereto is previously arranged is used, and an electrical conductive material or the like is formed on the support 1 by the screen printing method, sputtering evaporating method or the like, to form the working electrode 5, the counter electrode 6, and the detecting electrode 7. A preferred thin film electrode forming method for forming an electrical conductive layer of the biosensor A will be described in more detail in another embodiment.

Though the electrode part comprises the working electrode 5, the counter electrode 6 and the detecting electrode 7, the electrode part may comprise at least the working electrode 5 and the counter electrode 6. However, in order to perform a reliable measurement, it is preferable that the biosensor comprises the detecting electrode 7, since in this case a preferable biosensor, that is, a biosensor which is capable of performing a reliable measurement can be obtained.

Then, as shown in FIG. 1(c), a reagent is applied to the working electrode 5, the counter electrode 6, and the detecting electrode 7 as the electrode part formed on the support 1 to form a reagent layer 12, and the spacer 8 having the cutout part 9 for forming the specimen supply path is provided on the reagent layer 12. Then, the cover 13 is provided thereon. Here, one end of the cutout part 9 of the spacer 8 leads to the air hole 13a provided in the cover 13. The arrangement of the working electrode 5, the counter electrode 6, and the detecting electrode 7 which are formed on the support 1 is such that the counter electrode 6 is positioned at a position nearest to the inlet 9a of the specimen supply path, and the working electrode 5 and the detecting electrode 7 are positioned in the inner part therefrom. Respective areas of the working electrode 5, the counter electrode 6 and the detecting electrode 7 in the specimen supply path are defined by an area of the cutout part 9 of the spacer 8 and the interval 11 between the slits 4*a* and 4*b*. In the first embodiment, the slits 4*a* and 4*b* are provided so that the interval from a sensor tip to the slit 4*a* is equivalent to or larger than the interval 11 between the two slits 4*a* and 4*b*, and thus the area of the counter electrode 6 is equivalent to or larger than the area of the working electrode 5 in the specimen supply path.

Though the conductive layer 2 is formed on the whole surface of the support 1, it is also possible to form the conductive layer 2 not on the whole surface of the support 1 but on a part which is required for forming the electrode part. This will be described below.

Figure 2B:
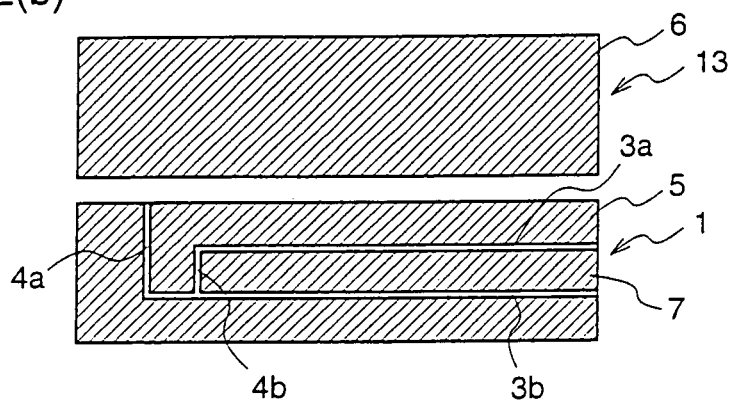
Figure 2C:
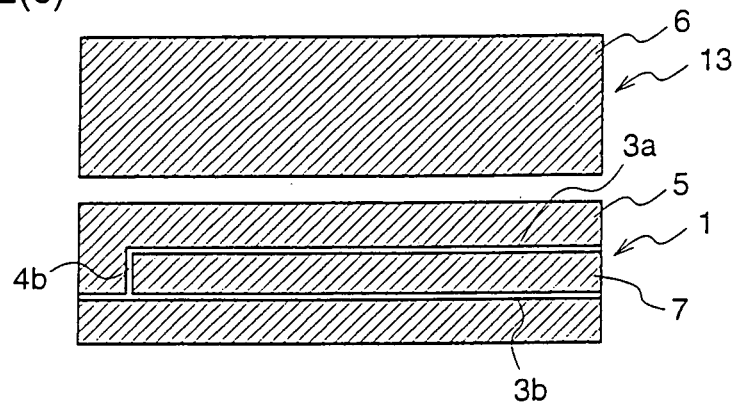

FIG. 2(*a*) is a schematic diagram illustrating how the electrodes of the above-described biosensor A are provided. Here, the conductive layer 2 required for forming the electrode part is provided only on the internal surface of the support 1, and the conductive layer 2 is not provided on the internal surface of the cover 13. The electrode part provided on the internal surface of the support 1 is divided into the counter electrode 6, the working electrode 5 and the detecting electrode 7 by the slits 3*a*, 3*b*, 4*a* and 4*b* being provided.

On the other hand, a method is also conceivable which provides the conductive layer 2 not only on the internal surface of the support 1 but also on the internal surface of the cover 13. An example of this case will be described briefly with reference to FIGS. 2(*b*) and 2(*c*). FIG. 2(*b*) illustrates a case where the conductive layer 2 provided on the internal surface of the cover 13 is taken as the counter electrode 6 as it is, and the conductive layer 2 provided on the internal surface of the support 1 is taken as the working electrode 5 and the detecting electrode 7 by the slits 3*a*, 3*b*, 4*a* and 4*b*. Though the conductive layer 2 is provided on the whole internal surface of the support 1, there is no need to use an unnecessary part as an electrode. That is, the conductive layer 2 is provided on the whole internal surface of the support 1 because in a process for providing the conductive layer 2, it is easier to provide the conductive layer 2 on the whole surface than in the case where the conductive layer 2 is provided on a part of the internal surface of the support 1. A hatching indicating the conductive layer 2 on the whole of the internal surface of the support 1 is shown in the figure, but there is no need to use all of this as the electrode. FIG. 2(*c*) schematically illustrates a case where the counter electrode 6 is provided on the internal surface of the cover 13, and the working electrode 5 and the detecting electrode 7 are provided on the internal surface of the support 1 as in FIG. 2(*b*), while the way in which the slits are provided on the support 1 is different from that shown in FIG. 2(*b*). That is, in FIG. 2(*c*), the slit 4*a* is omitted as compared with FIG. 2(*b*), while in this case it is required that the area of the counter electrode 6 is equivalent to or larger than the area of the working electrode 5 in the specimen supply path. When the number of slits provided on the support 1 is decreased as described above, the manufacture can be made more easily. Further, since the working electrode 5 is located at a position opposed to the counter electrode 6 in FIG. 2(*c*), the length of the specimen supply path is decreased to reduce the size, thereby enabling a measurement based on a trace quantity of specimen.

While in the embodiment 1 the division of the working electrode 5, the counter electrode 6, and the detecting electrode 7 is performed by employing the laser, it is also possible that a part of the conductive layer 2 is cut away by a jig with a sharp tip or the like, thereby to construct the electrode part. Further, while the screen printing method and the sputtering evaporating method are employed as the electrode part formation methods, the electrode part formation methods are not restricted to these methods.

As described above, according to the biosensor in the first embodiment of the present invention, the slits 3*a*, 3*b*, 4*a* and 4*b* are provided in the conductive layer 2 on the support 1, and the spacer 8 having the cutout part 9 is placed thereon, to define the respective electrode areas of the working electrode 5, the counter electrode 6 and the detecting electrode 7 on the specimen supply path easily and with a high accuracy.

Therefore, variation in response characteristics of respective biosensors can be reduced, thereby realizing a high-accuracy biosensor. Moreover, since in the present invention the electrode part is formed in a monolayer with an electrical conductive material such as noble metal for example gold or palladium and carbon as the material, it take no trouble of successively printing and laminating a silver paste, a carbon paste and the like on the support 1 as in the prior art, whereby it is possible to form the electrode part with a smooth surface by a simple method. Further, since the slits 4*a* and 4*b* are formed on the conductive layer 2 which is provided on the support 1 by the laser, it is possible to define the area of each electrode with a higher accuracy. The clearance between the respective electrodes can be considerably reduced to downsize the specimen supply path, thereby enabling the measurement based on a trace quantity of specimen while this could not be measured conventionally. Further, since the structures of the electrodes are very simple, a biosensor having the same performance can be easily formed.

Embodiment 2

A biosensor B according to the present invention will be described as a second embodiment.

Figure 4:
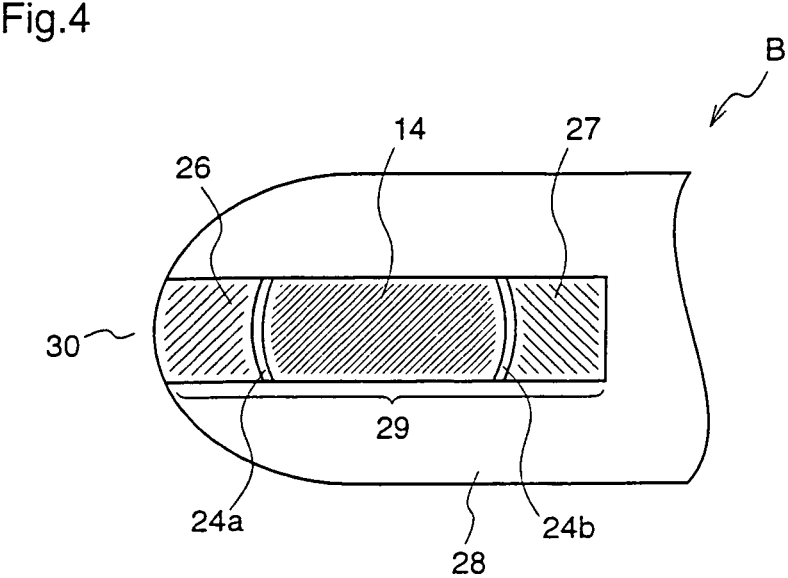
FIG. 4 is a diagram illustrating a specimen supply path of the biosensor according to the second embodiment.

FIGS. 3(*a*)-(*c*) are perspective views illustrating the biosensor B in the order of the manufacturing process, and FIG. 4 is a diagram illustrating a specimen supply path of the biosensor B.

First, the structure of the biosensor B will be described.

Numeral 21 denotes an insulating support which is composed of polyethylene terephthalate or the like. Numeral 22 denotes an electrical conductive layer which is formed on the whole surface of the support 21 and is composed of an electrical conductive material such as noble metal, for example gold or palladium, and carbon. Numerals 23*a*, 23*b*, 23*c* and 23*d* denote first slits which are provided on the electrical conductive layer 22. Numerals 25, 26 and 27 denote electrodes which are formed by dividing the electrical conductive layer 22 by the first slits 23*a*, 23*b*, 23*c* and 23*d*, i.e., a working electrode, a counter electrode, and a detecting electrode as an electrode for confirming whether a specimen is certainly drawn inside a specimen supply path. Numerals 24*a* and 24*b* denote second slits which define positions and areas on the electrodes where a reagent is applied. Numeral 28 denotes a spacer which covers the working electrode 25, the counter electrode 26, and the detecting electrode 27. Numeral 29 denotes a rectangular cutout part which is provided in the middle of an entering edge part of the spacer 28 to form a specimen supply path. Numeral 30 denotes an inlet of the specimen supply path. Numeral 14 denotes a reagent layer which is formed by applying a reagent including enzyme or the like to the working electrode 25, the counter electrode 26 and the detecting electrode 27 by dripping. Numeral 15 denotes a cover for covering the spacer 28. Numeral 16 denotes an air hole provided in the middle of the cover 15.

Next, a method for manufacturing the so-constructed biosensor B will be described.

As shown in FIG. 3(*a*), the electrical conductive layer 22 of a thin film of noble metal such as gold and palladium is formed over the whole of the support 21 by the sputtering method which is a method for forming a thin film. It is possible to form the electrical conductive layer 22 not on the whole surface of the support 21 but on only a part which is required for forming the electrodes.

Then, as shown in FIG. 3(b), the first slits 23a, 23b, 23c and 23d are formed on the electrical conductive layer 22 by employing the laser, to divide the electrical conductive layer 22 into the working electrode 25, the counter electrode 26 and the detecting electrode 27. Further, by employing the laser, the arc-shaped second slits 24a and 24b are formed on the electrical conductive layer 22 around a position where a reagent is dripped so as to surround the position.

Like in the first embodiment, the electrodes, the first slits 23a, 23b, 23c, and 23d, and the second slits 24a and 24b may be formed on the support 21 by the screen printing method, the sputtering method or the like, which employs a printing plate, a masking plate or the like, in which a pattern required for forming the electrical conductive layer 22 having the first slits 23a, 33b, 23c and 23d and the second slits 24a and 24b is previously arranged. Or, a part of the electrical conduction part 22 can be cut away by a jig with a sharp tip.

Then, as shown in FIG. 3(c), for example in case of a blood sugar sensor, a reagent which is composed of glucose oxidase as enzyme, potassium ferricyanide as an electron transfer agent and the like is dripped and applied to the working electrode 25, the counter electrode 26, and the detecting electrode 27. Since the part where the reagent is applied is a position which is surrounded by the second slits 24a and 24b, the second slits 24a and 24b can be used as marks of a place where the reagent is applied. Further, since the applied reagent is a liquid, it spreads out in a circular form taking a point where the reagent is applied by dripping as a center, but the second slits 24a and 24b serve as breakwaters and define the position and area of the reagent layer 14 so that the reagent is prevented from spreading across the second slits 24a and 24b. Therefore, the reagent layer 14 is formed at a prescribed position in a prescribed area.

Next, the spacer 28 having the cutout part 29 for forming the specimen supply path is placed on the electrodes, i.e., the working electrode 25, the counter electrode 26, and the detecting electrode 27. The specimen supply path lies in a state as shown in FIG. 4.

The cover 15 is provided on the spacer 28. One end of the cutout part 29 of the spacer 28 leads to the air hole 16 which is provided in the cover 15.

It is also possible to form the spacer 28 on the electrodes of the working electrode 25, the counter electrode 26, and the detecting electrode 27, and thereafter drip a reagent on a part of the working electrode 25, the counter electrode 26 and the detecting electrode 27, which is exposed from the cutout part 29, thereby to form the reagent layer 14.

According to this structure, when blood is supplied to the inlet 30 of the specimen supply path as a sample liquid which is a specimen, a certain amount of specimen is drawn into the specimen supply path due to capillary phenomenon by the air hole 16 and reaches the counter electrode 16, the working electrode 25 and the detecting electrode 27. The reagent layer 14 formed on the electrodes is dissolved by blood as the specimen, and an oxidation-reduction reaction occurs between the reagent and specific components in the specimen. Here, when the specimen fills the specimen supply path properly, an electrical change occurs between the counter electrode 26 and the detecting electrode 27. Thereby, it is confirmed that the specimen is drawn as far as the detecting electrode 27. The electrical change also occurs between the working electrode 25 and the detecting electrode 27, whereby it is also possible to confirm that the specimen is drawn as far as the detecting electrode 27. The reaction between the specimen and the reagent is promoted for a prescribed period of time after the specimen is drawn as far as the detecting electrode 27, and thereafter a prescribed voltage is applied to the working electrode 25 and the counter electrode 26 or between the counter electrode 26 and the detecting electrode 27. Since it is a blood sugar sensor, a current proportional to a glucose concentration is generated, and a blood sugar level can be measured by its value.

While in the second embodiment the blood sugar sensor is described as an example, it can be used as a biosensor other than the blood sugar sensor, by changing the components of the reagent 14 and the specimen. In addition, though the biosensor B which has the three electrodes is described in the second embodiment, the number of the electrodes may not be three. Further, while the second slits 24a and 24b are arc shaped, the shapes are not restricted to this shape as long as they can define the position and the area of the reagent layer and do not reduce the accuracy of the electrodes. For example, the slits may be straight lines or hook shaped.

As described above, the biosensor B according to the second embodiment is a biosensor for quantifying a substrate included in the sample liquid, which comprises an insulating support, plural electrodes which are formed by first slits provided on the electrical conductive layer formed on the whole or part of the surface of the insulating support, arc-shaped second slits provided in the electrical conductive layer to define the position and the area where the reagent is to be applied, a spacer having a cutout part which is provided on the electrodes to form a specimen supply path for supplying the sample liquid to the working electrode, a reagent layer including enzyme provided on the electrodes in the specimen supply path, and a cover which is provided on the spacer and has an air hole leading to the specimen supply path, and defines the spread of the applied reagent by the second slits. Therefore, when the reagent is applied on the electrodes for forming the reagent layer, the reagent spreads uniformly, and a reagent layer which is free from variations in the position and area is formed, resulting in an accurate measurement which is free from variations when the specimen is measured.

Embodiment 3

A specific method for manufacturing the above-described biosensors A and B will be further described. Here, the biosensors A and B are assumed a biosensor X collectively.

Figure 23:
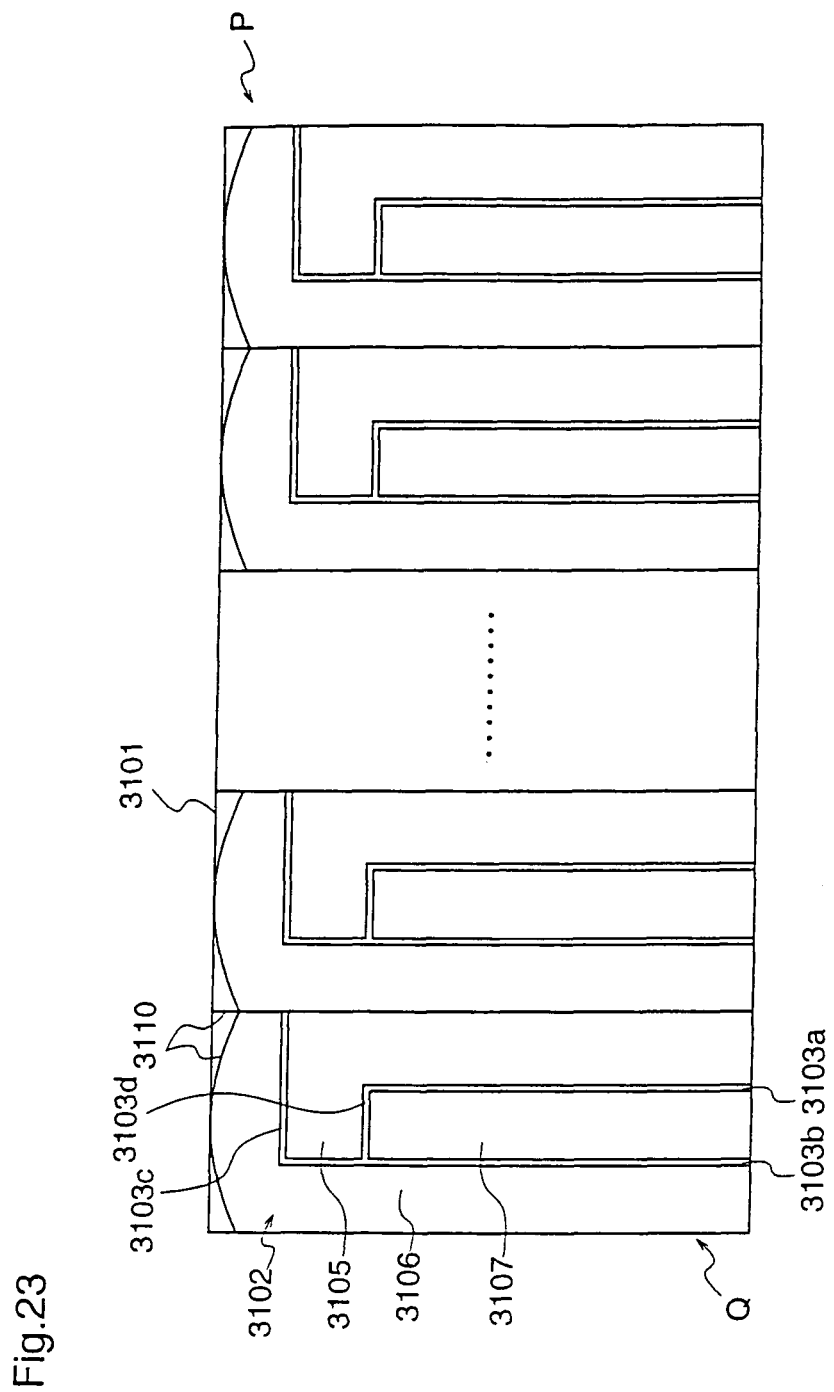
FIG. 23 is a top view illustrating a state where slits are formed in the electrical conductive layer which is provided on a sensor wafer according to the third embodiment.

FIG. 23 is a top view illustrating a state where the slits are formed on an electrical conductive layer provided on a surface of a sensor wafer P as a basis of the biosensor X.

Numeral 3102 denotes an electrical conductive layer composed of carbon, a metal material or the like, which is provided on the whole surface of a support 3101. Numerals 3103a, 3103b, 3103c and 3103d denote slits which are formed on the electrical conductive layer 3102. Numerals 3105, 3106 and 3107 denote electrodes which are formed by dividing the electrical conductive layer 3102 by the slits 3103a, 3103b, 3103c and 3103d, i.e., a working electrode, a counter electrode and a detecting electrode. Numeral 3110 denotes a cutting plane line showing a cutting position of the support. The sensor wafer P is a support in a state where the electrical conductive layer 3102 is formed on the support, and the electrical conductive layer 3102 is divided by the slits 3103a, 3103b, 3103c and 3103d to form electrodes of plural biosensors X, X, . . . , that is, the working electrodes 3105, the counter electrodes 3106, and the detecting electrodes 3107.

A manufacture of the biosensor X by employing the so-constructed sensor wafer P will be described with reference to figures.

First, the electrical conductive layer 3102 is formed on the whole surface of the band support 3101 by the sputtering method as a method for forming a thin film.

Next, as shown in FIG. 23, the slits 3103a, 3103b, 3103c and 3103d are formed by employing the laser in an area where each individual wafer Q of the electrical conductive layer 3102 formed on the support 3101 is formed, to divide the electrical conductive layer 3102 into the working electrode 3105, the counter electrode 3106, and the detecting electrode 3107, and the electrodes of plural biosensors X are formed in a row, thereby to form the sensor wafer P. Then, the electrodes of plural biosensors X which are formed in this process are cut on the cutting plane line 3110, and a reagent layer, a spacer and a cover (not shown here) are laminated on the electrodes of the biosensor X obtained by the cutting, thereby to form an individual biosensor.

Figure 24:
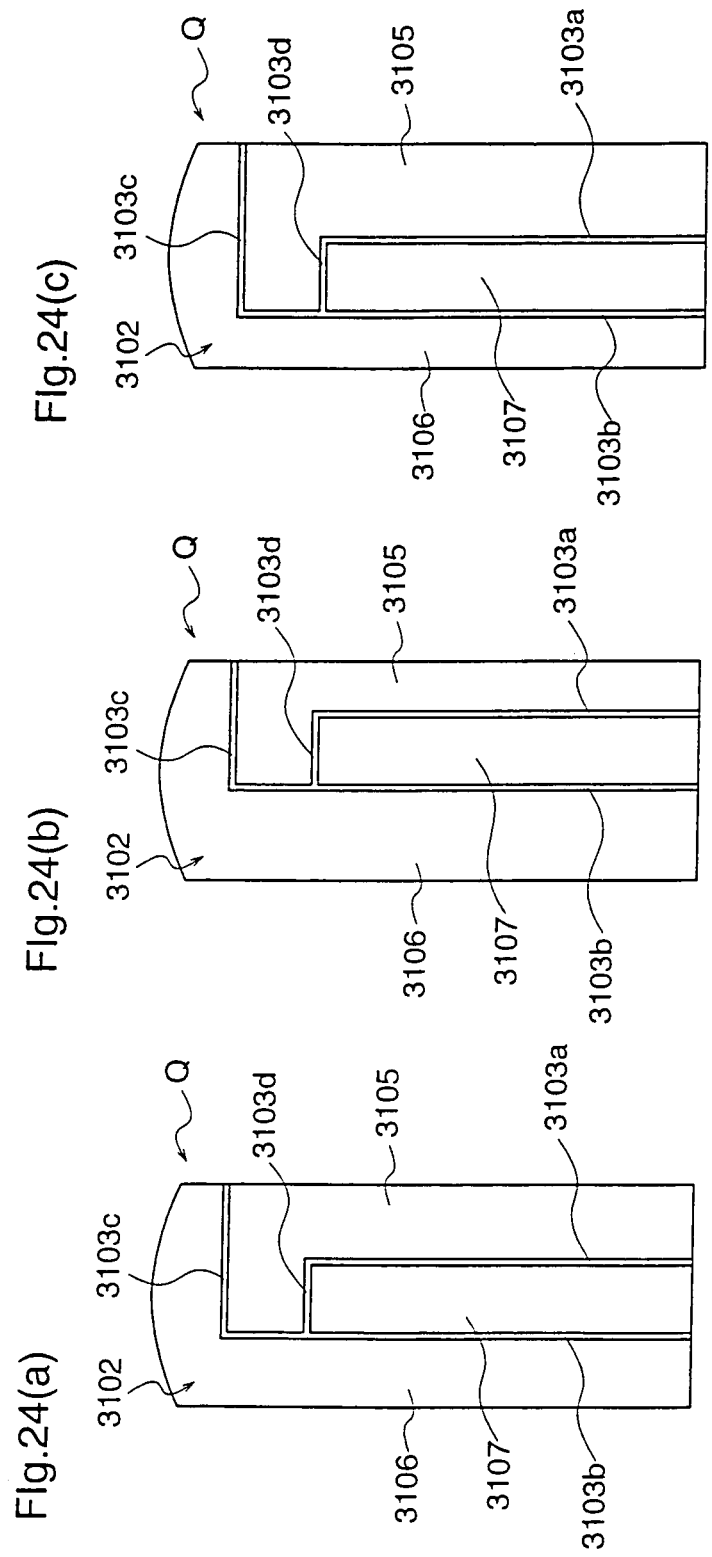
FIGS. 24(a)-(c) are top views illustrating states of electrodes of a biosensor in a manufacturing method according to the third embodiment.

However, the so-formed biosensor X has a problem in that when the plural biosensors are to be cut into individual biosensors, there are some cases where the cutting cannot be performed on the cutting plane lines, resulting in deviations from the cutting plane lines 3110. This will be described in more detail. FIG. 24(a) is a diagram illustrating states of the electrodes in a case where the cutting is correctly performed. FIG. 24(b) is a diagram illustrating states of the electrodes when the cutting position is deviated toward left from the cutting plane line 3110. FIG. 24(c) is a diagram illustrating states of the electrodes when the cutting position is deviated toward right from the cutting plane line 3110. Since the areas of the working electrode 3105 and the counter electrode 3106 are decided by the cutting position of the individual wafer Q, changes in the areas of the working electrode 3105 and the counter electrode 3106 occur when the cutting position is deviated from the cutting plane line 3110 as shown in the figures, resulting in variations in resistance values of the respective electrodes. Therefore, values of currents flowing the electrodes change, whereby the accuracy of the biosensor X get worse.

Here, a biosensor C according to the present invention, which has for its object to solve this problem will be described as a third embodiment.

Figure 5:
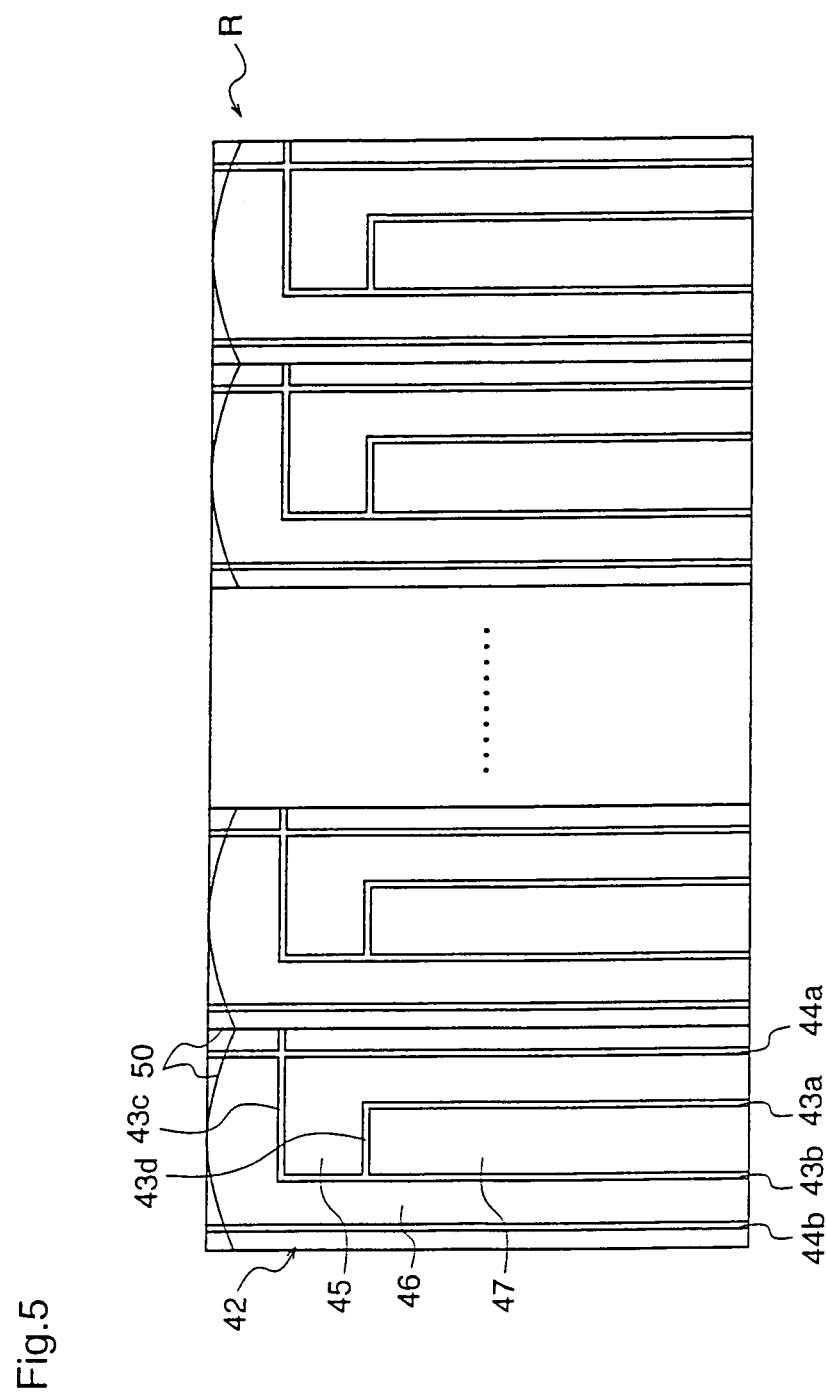
FIG. 5 is a top view illustrating a state where slits are formed in an electrical conductive layer of a biosensor according to a third embodiment.
Figure 6A:
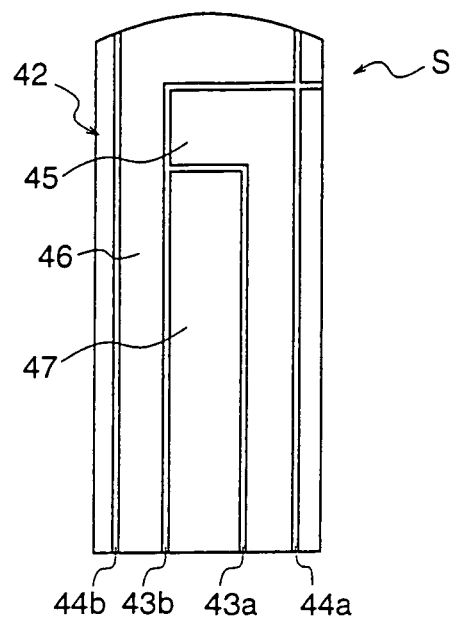
FIG. 6 are diagrams illustrating individual wafers of the biosensor according to the third embodiment.
Figure 6B:
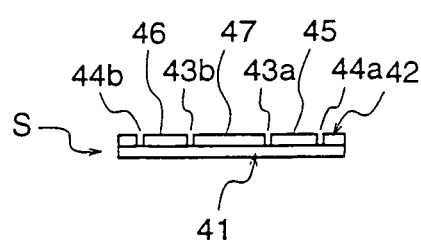
Figure 7:
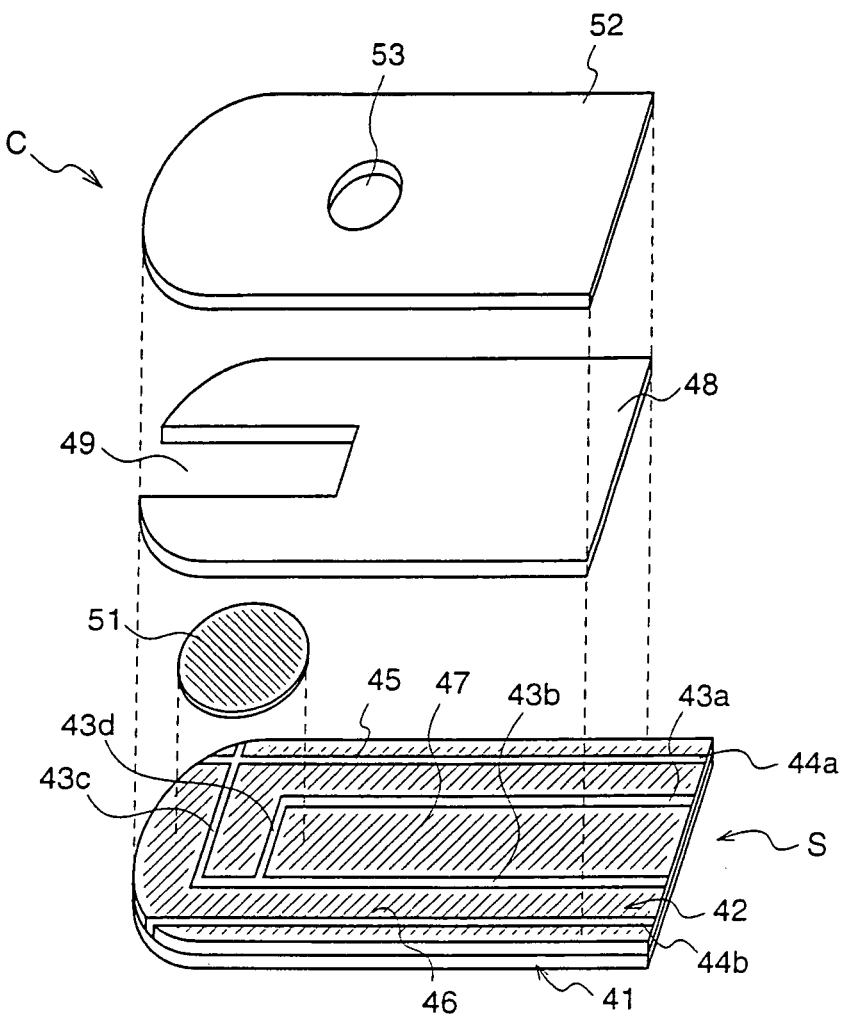
FIG. 7 is an exploded perspective view of the biosensor according to the third embodiment.
Figure 8A:
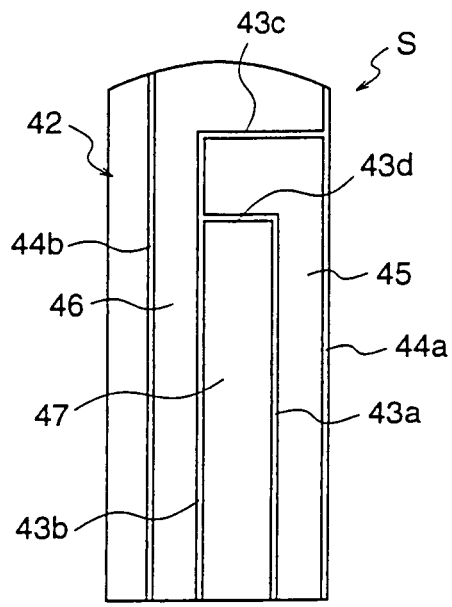
FIG. 8 are diagrams illustrating a state of electrodes of the biosensor according to the third embodiment.
Figure 8B:
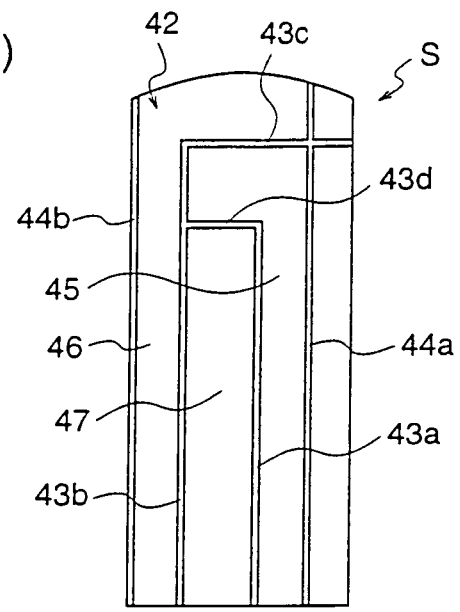

FIG. 5 is a top view illustrating a state where slits are formed on an electrical conductive layer which is provided on a surface of a sensor wafer R as a basis of the biosensor C. FIG. 6 are diagrams illustrating an individual wafer S of the biosensor C. FIG. 7 is a perspective view illustrating a manufacturing process of the biosensor C. FIG. 8 is a top view illustrating states of electrodes of the biosensor C.

Initially, component of the biosensor C will be described.

Numeral 41 denotes an insulating support which is composed of polyethylene terephthalate and the like. Numeral 42 denotes an electrical conductive layer which is formed on the whole surface of the support 41 and composed of an electrical conductive material such as noble metal, for example gold or palladium, and carbon. Numerals 43a, 43b, 43c and 43d denote first slits which are provided on the electrical conductive layer 42. Numerals 45, 46, and 47 denote electrodes which are formed by dividing the electrical conductive layer 42 by the first slits 43a, 43b, 43c and 43d, i.e., a working electrode, a counter electrode, and a detecting electrode as an electrode for confirming whether a specimen is surely drawn into a specimen supply path. Numeral 50 denotes a cutting plane line as a position where the support is cut. Numerals 44a and 44b denote third slits for defining the areas of the electrodes. Numeral 48 denotes a spacer which covers the working electrode 45, the counter electrode 46 and the detecting electrode 47. Numeral 49 denotes a rectangular cutout part which is provided in the middle of an entering edge part of the spacer 28 to form a specimen supply path. Numeral 51 denotes a reagent layer which is formed by applying a reagent including enzyme to the working electrode 45, the counter electrode 46 and the detecting electrode 47. Numeral 52 denotes a cover for covering the spacer 48. Numeral 53 denotes an air hole which is provided in the middle of the cover 52. The sensor wafer R is a support in a state where the electrical conductive layer 42 is formed in the support 41, and the electrical conductive layer 42 is divided by the first slits 43a, 43b, 43c and 43d as well as the third slits 44a and 44b to form electrodes of plural biosensors, that is, the working electrode 45, the counter electrode 46 and the detecting electrode 47. Further, an individual wafer S represents a state of each biosensor of the sensor wafer R.

A method for manufacturing the biosensor C will be described in the order of process.

Fist, the electrical conductive layer 42 is formed with a thin film of noble metal such as gold and palladium, over the whole band support 41 by the sputtering method.

Next, as shown in FIG. 5, the first slits 43a, 43b, 43c and 43d are formed by employing the laser in an area where each individual wafer S of the electrical conductive layer 42 formed on the support 41 is formed, to divide the electrical conductive layer 42 into the working electrode 45, the counter electrode 46, and the detecting electrode 47. Further, the third slit 44a on the right of the first slit 43a, and the third slit 44b on the left of the first slit 43b are formed by employing the laser at positions which are parallel to longitudinal sides of each biosensor after being cut and make the working electrode 45 and the counter electrode 46 have prescribed areas, thereby forming plural individual wafers S. FIG. 6(a) is a top view of the individual wafer S. FIG. 6(b) is a front view of the individual wafer S.

The electrical conductive layer 43 may be provided on the support 41 by the screen printing method, the sputtering method or the like, which employs a printing plate, a masking plate or the like in which a pattern required for forming the electrical conductive layer 42 having the first slits 43a, 33b, 43c and 43d as well as the third slits 44a and 44b is previously arranged, to form the first slits 43a, 43b, 43c and 43d as well as the third slits 44a and 44b. Or, these slits can be formed by cutting away a part of the electrical conduction part 42 by a jig with a sharp chip or the like.

Then, as shown in FIG. 7, for each wafer S, for example in the case of a blood sugar sensor, a reagent composed of glucose oxidase as enzyme, potassium ferricyanide as an electron transfer agent and the like is applied to the electrodes, i.e., the working electrode 45, the counter electrode 46 and the detecting electrode 47, to form the reagent layer 51.

Next, the spacer 48 having the cutout part 49 for forming the specimen supply path is provided on the electrodes, i.e., the working electrode 45, the counter electrode 46 and the detecting electrode 47.

The cover 52 is provided on the spacer 48. One end of the cutout part 49 of the spacer 48 leads to the air hole 53 provided in the cover 52.

It is also possible to form the spacer 48 on the electrodes, i.e., the working electrode 45, the counter electrode 46 and the detecting electrode 47, and thereafter apply a reagent on parts of the working electrode 45, the counter electrode 46 and the detecting electrode 47, which are exposed from the cutout part 49, thereby to form the reagent layer 51.

Then, plural biosensors which are formed by the above-described process are cut on the cutting plane lines 50 to form individual biosensors.

FIG. 8(*a*) is a diagram illustrating states of the electrodes when the cutting position is deviated toward left from the cutting plane line 50. FIG. 8(*b*) is a diagram illustrating states of the electrodes when the cutting position is deviated toward right from the cutting plane line 50. In any of the cases where the cutting position is deviated toward right and left, the areas of the working electrode 45 and the counter electrode 46 are already defined by the first slits and the third slits, whereby as shown in FIG. 8, the areas of the working electrode 45 and the counter electrode 46 are equal to those when the cutting is performed on the cutting plane line 50 shown in FIG. 6(*a*), as long as the cutting is performed between the third slits 44*a* and 44*b* of the adjacent biosensors.

Since the specimen measurement largely depends on the area or reaction of the working electrode 45, it is possible to provide only the third slit 44*a* which defines the area of the working electrode 45, without the third slit 44*b*.

In order to measure the specimen, when blood is supplied to the specimen supply path formed at the cutout part 49 of the spacer 48 as a sample liquid which is the specimen, a prescribed amount of specimen is drawn into the specimen supply path due to capillary phenomenon by the air hole 53, and reaches the counter electrode 46, the working electrode 45 and the detecting electrode 47. The reagent layer 51 formed on the electrodes is dissolved by the blood as the specimen, and oxidation-reduction reaction occurs between the reagent and specific components in the specimen. Here, when the specimen fills the specimen supply path properly, electrical changes occur between the counter electrode 46 and the detecting electrode 47. Thereby, it is confirmed that the specimen is drawn as far as the detecting electrode 47. The electrical changes also occur between the working electrode 45 and the detecting electrode 47, and thereby it is also possible to confirm that the specimen is drawn as far as the detecting electrode 47. The reaction between the specimen and the reagent is promoted for a prescribed period of time after the specimen is drawn as far as the detecting electrode 47, and thereafter a prescribed voltage is applied to the working electrode 45 and the counter electrode 46 or both of the counter electrode 46 and the detecting electrode 47. For example in the case of blood sugar sensor, a current which is proportional to the glucose concentration is generated and a blood sugar level can be measured by its value.

While in the third embodiment the blood sugar sensor is described as an example, this can be used as a biosensor other than the blood sugar sensor, by changing the components of the reagent 51 and the specimen. In addition, though the biosensor which has the three electrodes is described in the third embodiment, the number of the electrodes may be other than three as long as the areas of the electrodes are defined by the third slits. Further, it is sufficient that at least the area of the working electrode which greatly affects the measuring accuracy is defined by the third slits. The positions of the third slits are not restricted to those positions as long as they can define the areas of the electrodes. The shape of the biosensor may be other than that of the biosensor according to the third embodiment as long as it can define the areas of the electrodes by the third slits.

As described above, in the biosensor according to the third embodiment, the areas of respective electrodes are defined by the two third slits parallel to the longitudinal sides of the biosensor. Therefore, the areas of the respective electrodes are previously defined by the third slits and the areas of the respective electrodes are not changed according to the cutting position, resulting in no variation in the accuracy. Further, there is provided the reagent layer composed of the reagent which is to be reacted with the sample liquid, the spacer having the cutout part which forms the specimen supply path for supplying the sample liquid to the electrodes, and the cover which is placed on the spacer and has the air hole leading to the specimen supply path, whereby the sample liquid can be easily drawn into the specimen supply path. The electrical conductive layer is formed on the whole surface of the insulating support and is divided into plural electrodes by the first slits, thereby forming the high-accuracy electrodes and enhancing the working accuracy. Further, since the first slits and the third slits are formed by the laser, the high-accuracy processing is possible, thereby to define the areas of the respective electrodes with a high accuracy, as well as the clearance between the respective electrodes can be narrowed, thereby to downsize the biosensor.

Embodiment 4

A biosensor D according to the present invention will be described as a fourth embodiment.

Figure 22:
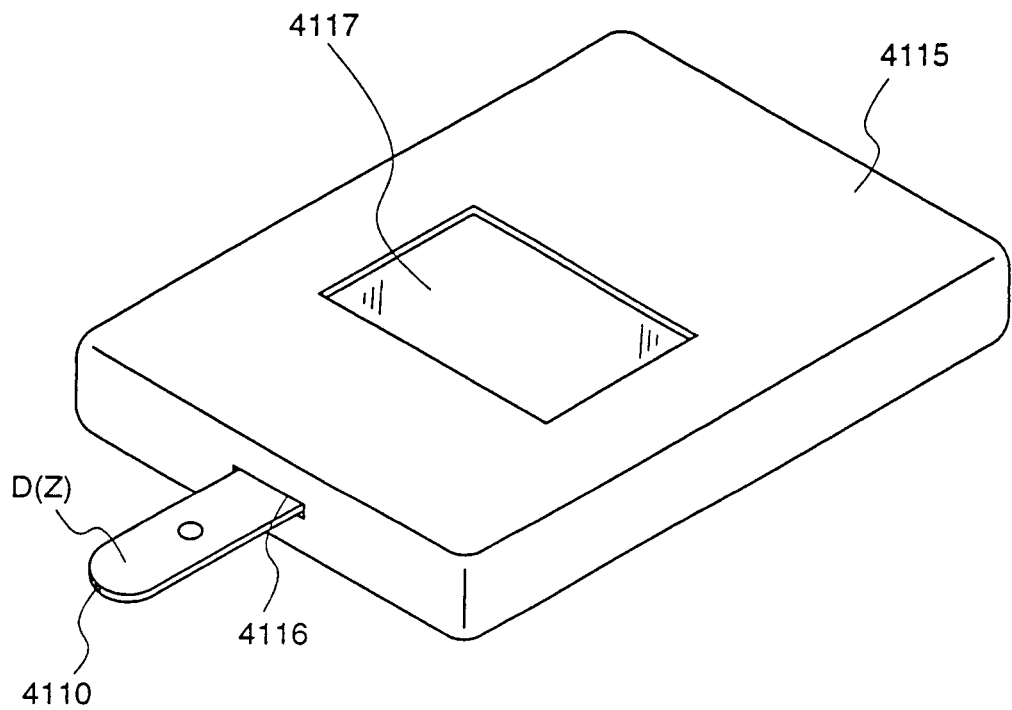
FIG. 22 is a diagram illustrating a state where a biosensor is inserted in a measuring device.

FIG. 9(*a*)-(*c*) are perspective views illustrating the biosensor D in the order of a manufacturing process. FIGS. 10(*a*)-(*h*) are top views exemplifying the formation of fourth slits of the biosensor D. FIG. 22 is a diagram illustrating a state where the biosensor D is inserted into a measuring device.

First, components of the biosensor D will be described.

Numeral 61 denotes an insulating support composed of polyethylene terephthalate or the like. Numeral 62 denotes an electrical conductive layer which is formed on the whole surface of the support 61 and is composed of an electrical conductive material such as a noble metal, for example gold or palladium, and carbon. Numerals 63*a*, 63*b*, 63*c* and 63*d* denote first slits provided in the electrical conductive layer 62. Numerals 65, 66, and 67 denote electrodes which are formed by dividing the electrical conductive layer 62 by the first slits 63*a*, 63*b*, 63*c* and 63*d*, i.e., a working electrode, a counter electrode, and a detecting electrode as an electrode for confirming whether the specimen is surely drawn into a specimen supply path, respectively. Numerals 64*a*, 64*b*, and 64*c* denote fourth slits which divide the counter electrode 66, the detecting electrode 67, and the working electrode 65, respectively. Numeral 68 denotes a spacer which covers the working electrode 65, the counter electrode 66, and the detecting electrode 67. Numeral 69 denotes a rectangular cutout part provided in the middle of an entering edge part of the spacer 68 to form a specimen supply path. Numeral 54 denotes a reagent layer which is formed by applying a reagent including enzyme or the like to the working electrode 65, the counter electrode 66, and the detecting electrode 67 by the dripping. Numeral 55 denotes a cover for covering the spacer 68. Numeral 56 denotes an air hole provided in the middle of the cover 55. Numerals 58, 59, and 57 denote correction parts provided at the end parts of respective electrodes, i.e., the working electrode 65, the counter electrode 66, and the detecting electrode 67. Numerals 71, 72, and 73 denote measuring parts which are on the periphery of the cover 55, of parts of the working electrode 65, the counter electrode 66, and the detecting electrode 67, respectively, which are exposed from the cover 55. D denotes a biosensor. Numeral 4115 denotes a measuring device in which the biosensor D is to be inserted. Numeral 4116 denotes an insertion opening of the measuring device 4115 into which the biosensor D is inserted. Numeral 4117 denotes a display part of the measuring device 4115 for displaying a measured result.

As shown in FIG. 9(a), the electrical conductive layer 62 of a thin film of a noble metal such as gold and palladium is formed by the sputtering method for manufacturing a thin film over the whole support 61. The electrical conductive layer 62 may not be formed on the whole surface of the support 61 but only on a part required for forming the electrodes.

Next, as shown in FIG. 9(b), the first slits 63a, 63b, 63c, and 63d are formed on the electrical conductive layer 62 by employing the laser, to divide the electrical conductive layer 62 into the working electrode 65, the counter electrode 66, and the detecting electrode 67. Further, the fourth slits 64a, 64b, and 64c are formed on the electrodes, i.e., the working electrode 65, the counter electrode 65, and the detecting electrode 67 by employing the laser. Here, the fourth slits 64a, 64b, and 64c divide all the electrodes, i.e., the working electrode 65, the counter electrode 66, and the detecting electrode 67, while there are for example eight kinds of combinations possible as shown in FIG. 10 as the manner in which the fourth slits 64a, 64b, and 64c are provided.

Figure 10A:
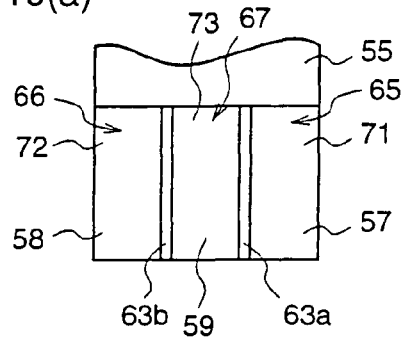
FIG. 10 are diagrams exemplifying a formation of second slits in the biosensor according to the fourth embodiment.
Figure 10B:
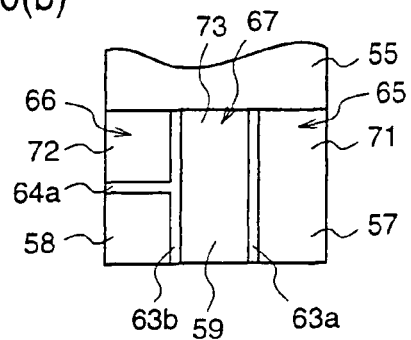
Figure 10C:
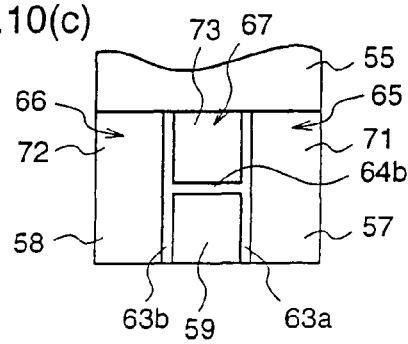
Figure 10D:
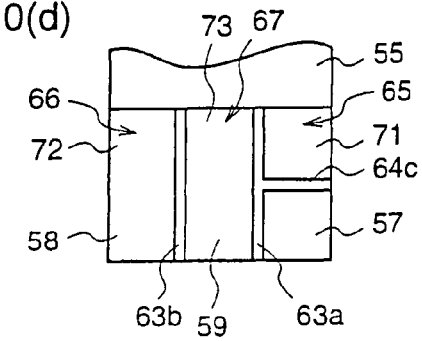
Figure 10E:
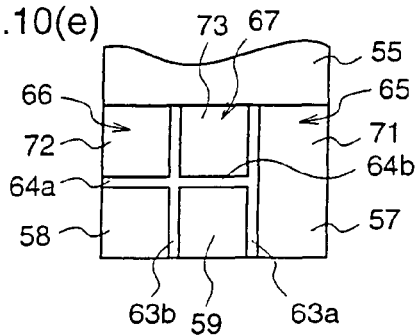
Figure 10F:
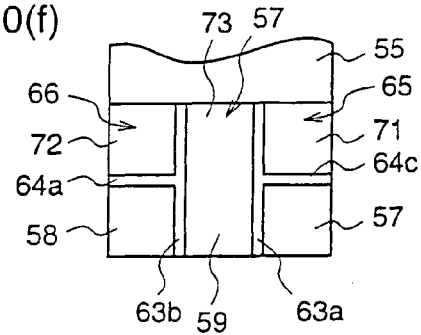
Figure 10G:
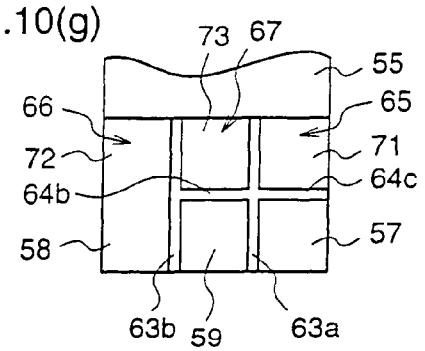
Figure 10H:
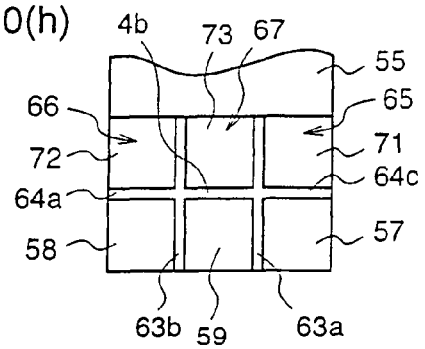

FIG. 10(a) illustrates a case where no fourth slit is provided. FIG. 10(b) illustrate a case where the fourth slit 64a is provided only in the counter electrode 66. FIG. 10(c) illustrate a case where the fourth slit 64b is provided only in the detecting electrode 67. FIG. 10(d) illustrates a case where the fourth slit 64c is provided only in the working electrode 65. FIG. 10(e) illustrates a case where the fourth slits 64a and 64b are provided in the counter electrode 66 and the detecting electrode 67. FIG. 10(f) illustrates a case where the fourth slits 64c and 64a are provided in the working electrode 65 and the counter electrode 66. FIG. 10(g) illustrates a case where the fourth slits 64c and 64b are provided in the working electrode 65 and the detecting electrode 67. FIG. 10(h) illustrates a case where the fourth slits 64c, 64a, and 64b are provided in all the electrodes, i.e., the working electrode 65, the counter electrode 66, and the detecting electrode 67.

The combinations of the fourth slits 64a, 64b, and 64c enable the measuring device 4115 to discriminate information of correction data for correcting a difference in the output characteristics for each production lot. For example, in the case of FIG. 10(a) where no fourth slit is provided, it is assumed a biosensor which has output characteristics of the production lot number "1". In the case of FIG. 10(b) where the fourth slit 64a is provided only in the counter electrode 66, it is assumed a biosensor which has output characteristics of the production lot number "2".

The electrodes, the first slits 63a, 63b, 63c and 63d, and the fourth slits 64a, 64b and 64c may be formed on the support 61 by the screen printing method, the sputtering method or the like that employs a printing plate, a masking plate or the like in which a pattern required for forming the electrical conductive layer 62 having the first slits 63a, 63b, 63c and 63d as well as the fourth slits 64a, 64b and 64c is previously arranged. Or, this may be formed by cutting away a part of the electrical conduction part 62 by a jig with a sharp tip. Further, the fourth slits 64a, 64b, and 64c may be formed after the biosensor 164 is completed and its output characteristics are checked, thereby reliably performing selection for each production lot.

Next, as shown in FIG. 9(c), for example in the case of a blood sugar sensor, a reagent composed of glucose oxidase as enzyme, potassium ferricyanide as an electron transfer agent or the like is applied to the working electrode 65, the counter electrode 66, and the detecting electrode 67 by the dripping.

Then, the spacer 68 having the cutout part 69 for forming the specimen supply path is placed on the electrodes, i.e., the working electrode 65, the counter electrode 66, and the detecting electrode 67.

The cover 54 is placed on the spacer 68. One end of the cutout part 56 of the spacer 68 leads to the air hole 56 provided in the cover 55.

It is also possible to form the spacer 68 on the electrodes of the working electrode 65, the counter electrode 66 and the detecting electrode 67, and thereafter drip the reagent on parts of the working electrode 65, the counter electrode 66 and the detecting electrode 67, which are exposed from the cutout part 69, thereby to form the reagent layer 54.

When the specimen is to be measured by the biosensor, the biosensor D is initially inserted to the insertion opening 4116 of the measuring device 4115 as shown in FIG. 22. When blood is supplied to the inlet of the specimen supply path as a sample liquid of the specimen, a prescribed amount of specimen is drawn into the specimen supply path due to capillary phenomenon by the air hole 56 and reaches the counter electrode 66, the working electrode 65, and the detecting electrode 67. The reagent layer 54 formed on the electrodes is dissolved by the blood as the specimen, and oxidation-reduction reaction occurs between the reagent and specific components in the specimen. Here, when the specimen fills the specimen supply path properly, electrical changes occur between the counter electrode 66 and the detecting electrode 67. Thereby, it is confirmed that the specimen is drawn as far as the detecting electrode 67. Here, the electrical changes also occur between the working electrode 65 and the detecting electrode 67, and thereby it is also possible to confirm that the specimen is drawn as far as the detecting electrode 67. The reaction between the specimen and the reagent is promoted for a prescribed period of time after the specimen is drawn as far as the detecting electrode 67, and thereafter a prescribed voltage is applied to the working electrode 65 and the counter electrode 66 or both of the counter electrode 66 and the detecting electrode 67. In the case of a blood sugar sensor, a current proportional to the glucose concentration is generated and the measuring device 4115 measures its value. The electrical changes in the respective of the above-described working electrode 65, counter electrode 66, and detecting electrode 67 are sensed by the measuring parts 71, 72, and 73.

Also, the measuring device 4115 checks whether the respective electrodes of the biosensor D, that is, the working electrode 65, the counter electrode 66, and the detecting electrode 67 are divided by the fourth slits 64a, 64a, and 64b. For example, when the electrical conduction between the measuring part 71 and the correction part 57 is checked, it can be seen whether the fourth slit 64c has been formed. Similarly, when electrical conduction between the measuring part 72 and the correction part 58 is checked, it can be seen whether the fourth slit 64a has been formed, and when electrical conduction between the measuring part 73 and the correction part 59 is checked, it can be seen whether the fourth slit 64b has been formed. For example, when the fourth slit is not formed on any electrodes, it is in a state shown in FIG. 10(a) where the biosensor is of the production lot number "1", and thus the measuring device 4115 obtains a blood sugar level on the basis of the correction data corresponding to the output characteristics of the production lot number "1" which are previously stored and the measured current value, and displays the blood sugar level at the display part 4117. Similarly, when the fourth slit 64a is formed only in the counter electrode 66, a blood sugar level is obtained on the basis of the correction data corresponding to the output characteristics of the production lot number "2" and the measured current value, and the obtained blood sugar level is displayed at the display part 4117.

While in the fourth embodiment a blood sugar sensor is described as an example, it can be used as a biosensor other than the blood sugar sensor, for example as a lactic acid sensor or a cholesterol sensor, by changing the components of the reagent layer 54 and the specimen. Also in such cases, when it is made possible for the measuring device to discriminate information of correction data corresponding to the output characteristics of the lactic acid sensor or the cholesterol sensor according to the position of the fourth slits, the measuring device 4115 obtains a measured value from the previously stored correction data corresponding to the output characteristics of the lactic acid sensor or the cholesterol sensor and a current value, to display the value at the display part 4117.

While the biosensor having the three electrodes is described in the fourth embodiment, the number of the electrodes may be other than three. Further, plural fourth slits may be provided on a single electrode.

As described above, in the biosensor D according to the fourth embodiment, the production lot of the biosensor can be discriminated according to the electrodes on which the fourth slits which divides the respective electrodes are formed. Therefore, the measuring device can discriminate necessary correction data by inserting the biosensor therein, and thus there is no need for an operator to input correction data by employing a correction chip or the like, resulting in elimination of troubles and a prevention of operational errors. Further, there is provided the reagent layer composed of a reagent which is to be reacted with the sample liquid, the spacer having the cutout part which forms the specimen supply path for supplying the sample liquid to the electrodes, and the cover which is placed on the spacer and has the air hole leading to the specimen supply path, whereby the sample liquid can be easily drawn into the specimen supply path. The electrical conductive layer is formed on the whole surface of the insulating support and is divided into plural electrodes by the first slits, thereby forming high-accuracy electrodes and enhancing the measuring accuracy. Further, since the first slits and the fourth slits are formed by the laser, a high-accuracy processing is possible, whereby the areas of the respective electrodes can be defined with a high accuracy, as well as the clearance between the respective electrodes can be narrowed, thereby to downsize the biosensor.

In any of the above-described biosensors A, B, C, and D according to the first to fourth embodiments, it is more preferable that each slit provided on the electrical conductive layer is processed by the laser, the width of each slit is 0.005 mm-0.3 mm, and the depth of each slit is equal to or larger than the thickness of the electrical conductive layer.

Further, it is preferred that the reagent layer provided in any of the biosensors A, B, C, and D should include enzyme, an electron transfer agent, or a hydrophilic polymer.

In addition, it is preferable that the insulating support employed in any of the biosensors A, B, C, and D is made of a resin material.

Embodiment 5

A thin film electrode forming method of the present invention will be described as a fifth embodiment with reference to the figures. When the thin film electrode method described in the fifth embodiment is applied when the electrode parts of any of the biosensors A, B, C, and D according to the above-described first to fourth embodiments are formed, a biosensor of the present invention can be obtained.

Figure 11:
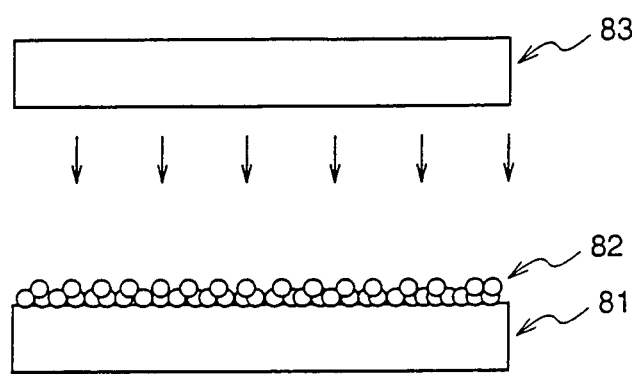
FIG. 11 is a schematic diagram showing the concept of a biosensor which is formed in a fifth embodiment.

FIG. 11 is a schematic diagram showing a state of a biosensor, where a thin film electrode is formed by implementing the thin film electrode forming method according to this embodiment and a reaction reagent layer are laid out thereon.

Figure 25:
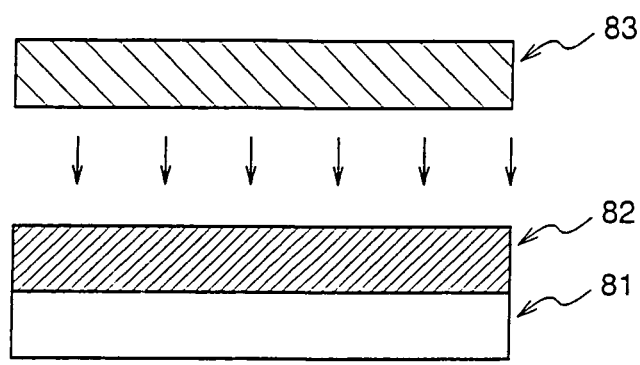
FIG. 25 is a diagram illustrating the concept of a cross-sectional structure of a conventional biosensor.

This biosensor differs most from the conventional biosensor shown in FIG. 25 in that a surface roughening processing is performed on the surface of an insulating resin support 81 of polyethylene terephthalate, polycarbonate or the like, to enhance adhesion between the support 81 and an electrode layer 82 as well as between the electrode layer 82 and a reaction reagent layer 83. It also differs in that a material constituting the electrode layer 82 is a simple substrate material composed of a noble metal or carbon, and the thickness of the electrode layer 82 is controlled within 3-100 nm.

Hereinafter, a specific method of the surface roughening processing for the surface of the support 81 will be described. Materials suitable for the support 81 are polyethylene terephthalate, polycarbonate, polybutylene terephthalate, polyamide, polyvinyl chloride, polyvinylidene chloride, polyimide, nylon, or the like.

Initially, the support 81 is placed in a vacuum chamber, and thereafter is subjected to a vacuum evacuation as far as a prescribed degree of vacuum (this can be within a range of $1\times10^{-1}$ to $3\times10^{-3}$ pascals). Thereafter, when the vacuum chamber is filled up with an inert gas (the degree of vacuum after the filling is within a range of approximately 0.1 to 10 pascals), and a high-frequency voltage of approximately 0.01 to 5 KV is applied thereto, the inert gas is excited and ionized, and is slammed onto the surface of the support 81. These ions have high kinetic energies, and enough surface roughening effects can be obtained by the high-frequency voltage application in quite a short period of time (approximately 0.1 to 10 seconds). Further, similar surface roughening effects can be obtained not only by the high-frequency voltage application but also by a DC voltage application or the like.

Nitrogen as well as rare gases such as argon, neon, helium, krypton and xenon can be employed as the inert gases. It also is possible to roughen the surface of the support 81 in the case where an activated gas (reactive gas) as typified by oxygen is used. However, in this case an oxide coat is formed on the surface of the support 81, accordingly there are possibilities that the electrode characteristics and sensor response characteristics are adversely affected, and thus it is not so desirable.

Next, a description will be given of a method for forming a thin film electrode layer composed of a conductive substance on the surface of the support 81 which has been subjected to the surface roughening processing.

Like in the surface roughening processing for the surface of the support 81, it is subjected to the vacuum evacuation to a prescribed degree of vacuum (it can be within a range of $1\times10^{-1}$ to $3\times10^{-3}$ pascals). Thereafter, the vacuum chamber is filled up with an inert gas (the degree of vacuum after the filling is within a range of approximately 0.1 to 10 pascals), and a high-frequency voltage of approximately 0.01 to 5 KV is applied thereto, whereby the inert gas is excited and ionized. The ionized gas is collided against a target plate composed of a conductive material, whereby atoms of the conductive substance are beaten out and then deposited as a film on the support 81, thereby forming a thin film electrode layer. It is also possible that the vacuum evacuation is performed and thereafter the conductive substance is heated and evaporated so as to be deposited as a film on the support 81, thereby forming a thin film electrode layer. A typical one of the former manufacturing method is the sputtering evaporation, and a typical one of the latter is the vacuum evaporation.

A material of the conductive material for forming the target plate may be a noble metal such as palladium, platinum, gold, and ruthenium, or carbon, and these simple substrate materials are employed as an electrode material, thereby to enable a stable electrode mass manufacture which hardly depends on manufacturing conditions and which has a smaller difference among material lots.

Figure 12:
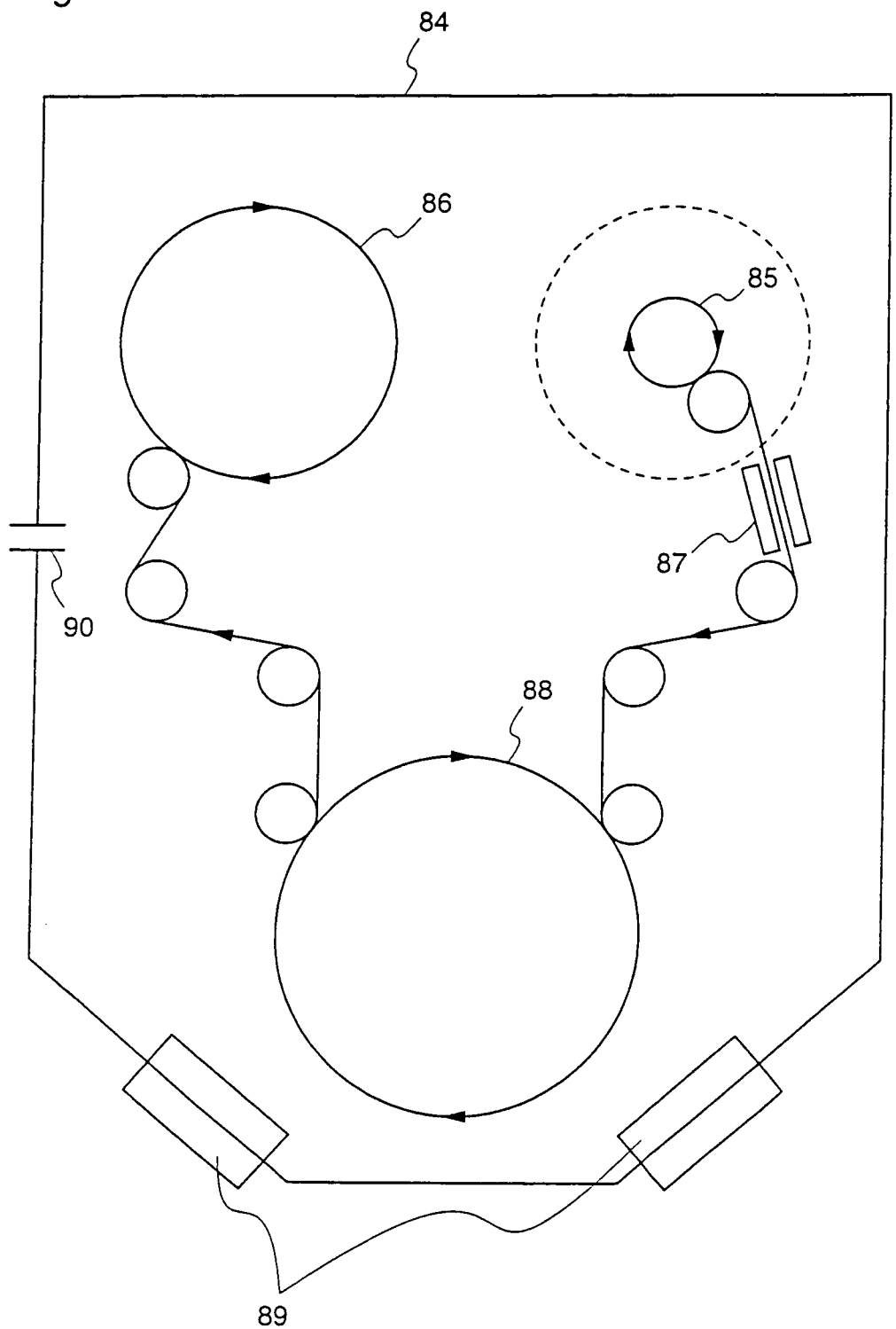
FIG. 12 is a schematic diagram showing the concept of an apparatus for forming a thin film electrode in the fifth embodiment.

It is possible to perform the support surface roughening process and the thin film electrode formation process discontinuously in independent spaces. However, by performing the process for roughening the surface of the support 81 and the process of forming the thin film electrode continuously in the same space as shown in FIG. 12, a reduction in manufacturing man-hours, as well as an enhancement in the productivity due to the enhancement in production tact, and a reduction in costs of the biosensors attendant thereupon can be realized. FIG. 12 is a schematic structure diagram illustrating a manufacturing process of the thin film electrode in the fifth embodiment. In the figure, numeral 84 denotes a vacuum chamber, numeral 85 denotes a support delivery roll, numeral 86 denotes a support take-up roll, numeral 87 denotes a surface roughening processing electrode, numeral 88 denotes a cooling roller, numeral 89 denotes a cathode/target, and numeral 90 denotes a gas introduction inlet.

In the case where two processes are performed continuously in the same space as described above, it is difficult to perform a vacuum evaporation, and thus it is effective to perform a high-frequency sputtering evaporation, a bias sputtering evaporation, an asymmetric AC sputtering evaporation, an ion plating and the like.

It goes without saying that a reduction in manufacturing costs is enabled by making the thickness of the electrode layer as thin as possible, while by reflecting the roughened surface of the support as a roughened surface for the surface of the electrode layer as it is, the adhesion between the electrode layer 82 and the reaction reagent layer 83 composed of enzyme, an electron transfer agent and the like is considerably enhanced. In order to reflect the roughened surface of the support 81 surface as a roughened surface of the electrode layer surface, the thickness of the electrode layer is required to be 100 nm or less, and it is desirable that the thickness of the electrode layer should be 3-50 nm to provide higher-performance thin film electrode and biosensor.

A further description will be given of the above-described thin film electrode forming method according to the fifth embodiment with reference to a specific experimental example.

A high-frequency voltage having a frequency of 13.56 MHz at 100 W-output is applied onto the insulating support 81 composed of polyethylene terephthalate for a prescribed period of time, to perform the surface roughening processing, and thereafter a noble metal thin film electrode is formed by forming palladium with the thickness of approximately 10 nm on the roughened support under the same condition.

Figure 18:
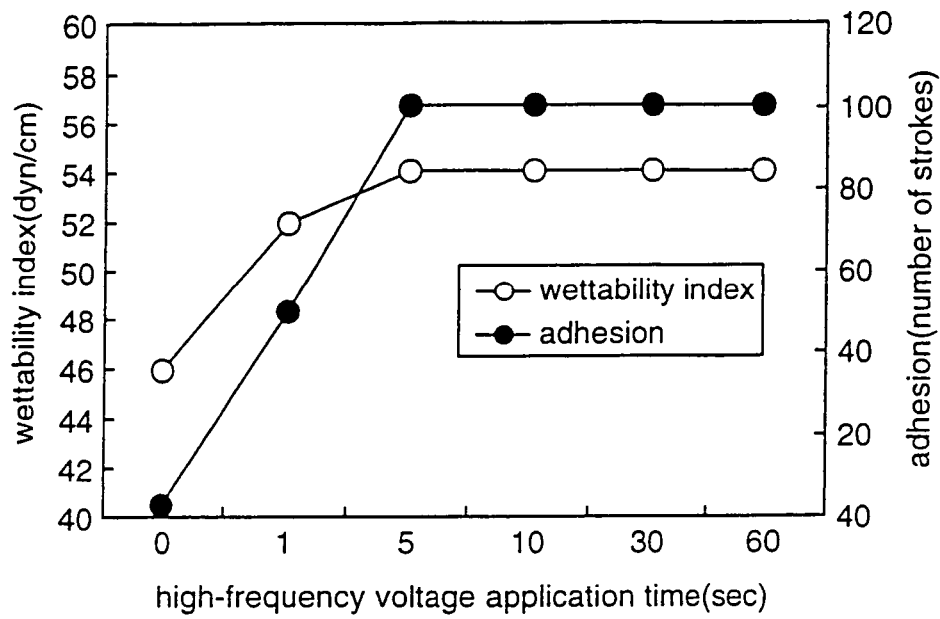
FIG. 18 is a diagram illustrating changes in wettability index (surface tension) of a support surface and an adhesion between an electrode layer and the support.

FIG. 18 illustrates the changes in a wettability index (surface tension) of the support surface and the adhesion between the electrode layer and the support surface due to the surface roughening processing depending on the time for applying the high-frequency voltage from 0 to 60 seconds (0 second shows a state where the surface roughening processing is not performed), and this figure illustrates that surface roughening of the support surface is realized by the application for more than 5 seconds and the surface wettability as well as the adhesion between the electrode layer and the support are enhanced. This embodiment is the result which is obtained at a high-frequency voltage of 100 W, and a further reduction in the processing time is enabled by increasing the high-frequency voltage.

The adhesion valuation here is executed in conformance with JIS5600-5-10 (paint ordinary test method: mechanical property of a paint film: a wear resistance), and a numeric value of the adhesion in the figure is indicated by the number of times of stroke reciprocation up to a time when a palladium thin film is worn out and the support surface goes in an exposed state, and a larger numeric value indicates a higher adhesion.

Figure 19:
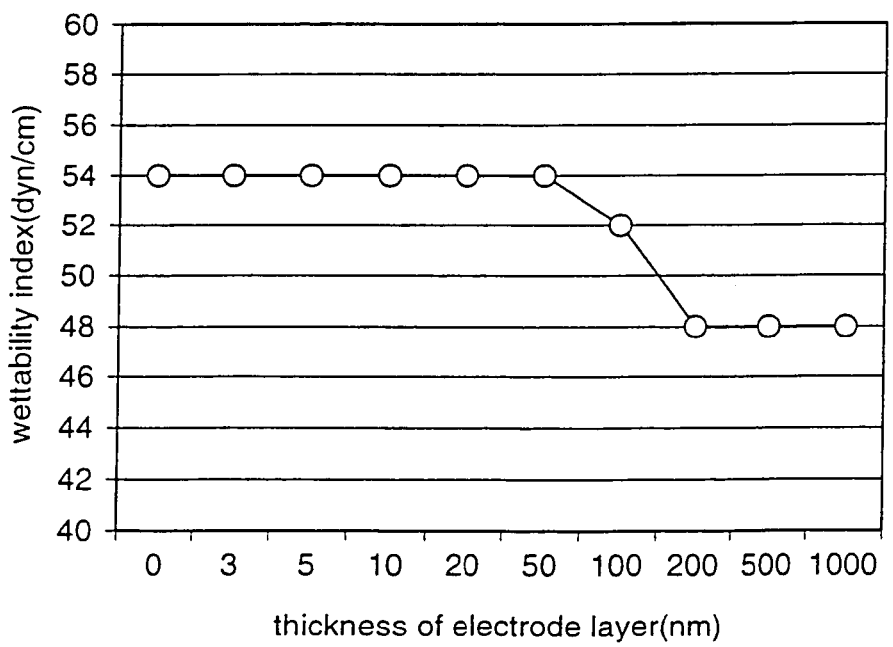
FIG. 19 is a diagram illustrating a relationship between a thickness of a palladium thin film and the wettability index (surface tension) of the electrode surface.

FIG. 19 illustrates a relationship between the thickness of the palladium thin film and the wettability index (surface tension) of the electrode surface. The conditions of the surface roughening processing of the support surface are adjusted arbitrarily within a range where a high-frequency voltage is 100 W, the application time is 5 seconds, and the thickness of the palladium layer is 5 to 1000 nm. As apparent from FIG. 19, in a range where the thickness of the palladium layer is 3 to 50 nm, the wettability index of the support surface subjected to the surface roughening processing is kept in 54 dyn/cm, and when it exceeds 100 nm the wettability index is decreased to 48 dyn/cm, and thereafter it is kept stable at that value. This indicates that the roughened surface of the support surface reflects the roughened surface of the electrode surface up to the thickness 100 nm, while it reflects the wettability of the electrode material itself (palladium in the embodiment) in the case of the thickness exceeding 100 nm.

Next, the reaction reagent layer including carboxymethyl cellulose as a hydrophilic polymer, glucose oxidase (GOD) as enzyme, and potassium ferricyanide as an electron transfer agent is formed on the thin film electrode which is formed under the above-described conditions, whose thickness of the palladium layer is 10 nm, and thereafter a biosensor for measuring the blood sugar level as in FIG. 1, in which a spacer and a cover are laid out is manufactured.

Figure 20:
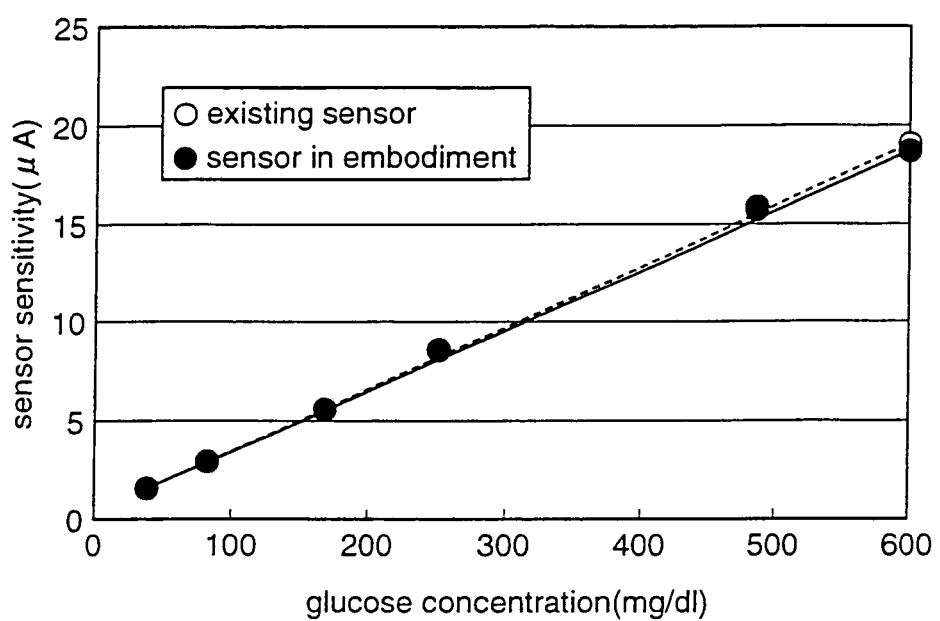
FIG. 20 is a diagram in which sensor sensitivities in a blood glucose concentration of 40-600 mg/dl are compared.

FIG. 20 is a diagram in which the sensor sensitivities in blood glucose concentrations of 40-600 mg/dl are compared. The blood is drawn into a capillary tube, then a reaction between a reaction reagent and glucose in the blood is promoted for about 25 seconds, and thereafter a prescribed voltage is applied between terminals of a working electrode and a counter electrode. The sensor sensitivity here is a current value which is obtained 5 seconds after the application of the prescribed voltage. Since the conventional sensor and the sensor in the embodiment have different electrode materials, an applied voltage is 0.5 V for the conventional carbon paste electrode while it is 0.2 V for the palladium thin film electrode in the embodiment.

Further, the measuring number is n=10 in each concentration range. As apparent from FIG. 20, it is confirmed that the sensor in the embodiment which is not subjected to a polishing processing or heat processing for the electrode surface has an equivalent or higher sensitivity as compared with a sensor which is subjected to the polishing processing or heat processing, which was conventionally regarded as required to enhance the sensor sensitivity.

The repeatabilities (C.V. values) of the ten-times measuring are compared in (table 1). From the result shown in the table, it is confirmed that the sensor in the embodiment has an excellent accuracy, with variations in individual sensors being reduced, while a conventional sensor has its CV value remarkably deteriorated due to the polishing processing variations or the like.

TABLE 1

| Glucose concentration | Conventional sensor | Sensor in embodiment |
|---|---|---|
| 40 mg/dl | 15.25% | 3.89% |
| 82 mg/dl | 6.15% | 2.87% |
| 165 mg/dl | 3.89% | 2.43% |

TABLE 1-continued

| Glucose concentration | Conventional sensor | Sensor in embodiment |
|---|---|---|
| 248 mg/dl | 3.24% | 1.80% |
| 485 mg/dl | 3.79% | 2.16% |
| 600 mg/dl | 3.28% | 1.65% |

Embodiment 6

Hereinafter, a quantification method of quantifying a substrate and a quantification apparatus for quantifying a substrate, which employ any of the biosensors A, B, C, and D, for which the electrical conductive layers are formed by employing the above-described thin film electrode forming method according to the fifth embodiment will be described. while the biosensor A as described in the first embodiment is used as a biosensor employed in a following description, the biosensor to be used is not restricted thereto.

Figure 13:
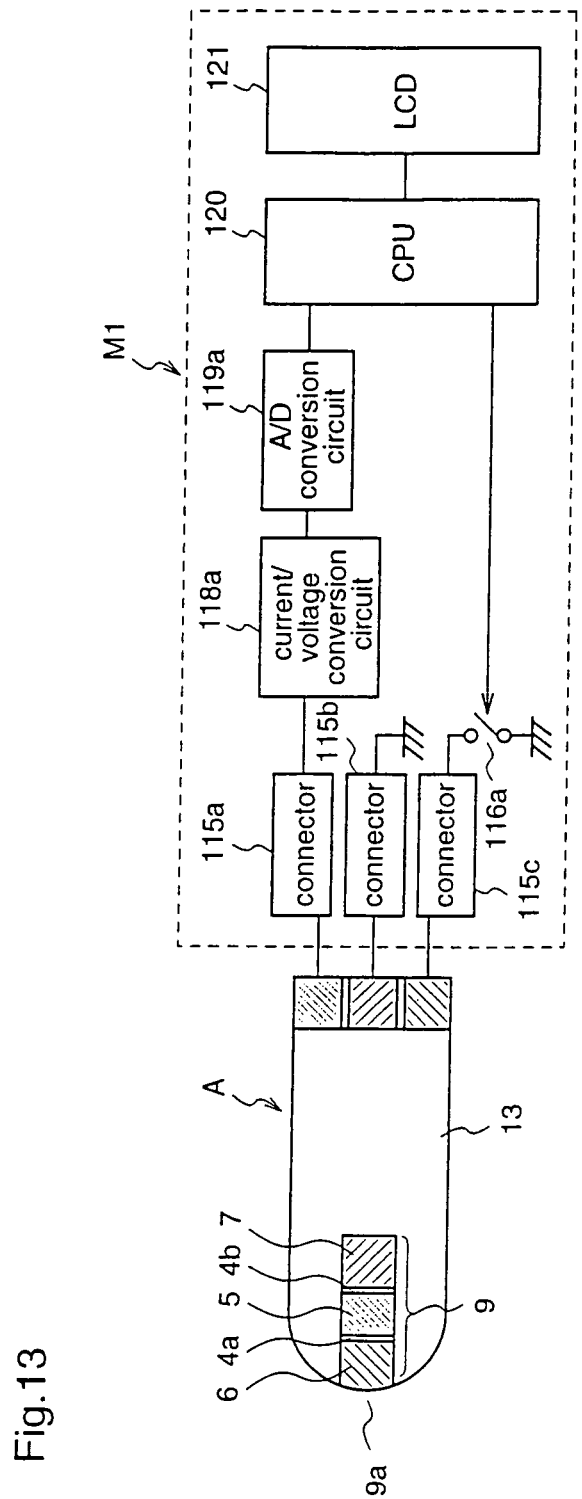
FIG. 13 is a diagram illustrating structures of a biosensor and a quantification apparatus according to a sixth embodiment.

FIG. 13 is a diagram illustrating structures of the biosensor and the quantification apparatus which is employed in the quantification method employing the biosensor. In the figure, the same reference numerals as those shown in FIG. 1 denote the same or corresponding parts.

It is a system in which the biosensor A is used in a state where it is connected to a quantification apparatus M1, and the quantification apparatus M1 measures the amount of an included substrate from a specimen supplied to the biosensor A.

In the quantification apparatus M1, numerals 115a, 115b, and 115c denote connectors connected to a working electrode 5, a detecting electrode 7, a counter electrode 6 of the biosensor A, respectively, numeral 116a denotes a switch provided between the connector 115c and the ground (which means a constant potential electrodeposition and can be not always "0". The same goes for in the present specification.), numeral 118a denotes a current/voltage conversion circuit which is connected to the connector 115a and converts a current flowing between the working electrode 6 and other electrode into a voltage to be output, numeral 119a denotes an A/D conversion circuit which is connected to the current/voltage conversion circuit 118a and converts a voltage value from the current/voltage conversion circuit 118a into a pulse, numeral 120 denotes a CPU which controls ON/OFF of the switch 116a and calculates the amount of a substrate included in a specimen based on the pulse from the A/D conversion circuit 119a, and numeral 121 denotes a LCD (liquid crystal display) which displays a measured value calculated by the CPU 20.

Hereinafter, a description will be given of the operations of the biosensor A and the quantification apparatus M1 when the amount of the substrate included in a specimen is measured by the quantification method employing the biosensor according to the sixth embodiment of the present invention.

First, when the biosensor A is connected to the connectors 115a-115c of the quantification apparatus M1, the switch 116a is turned off under the control of the CPU 120, leading to a non-connection state between the counter electrode 6 and the ground, and a prescribed voltage is applied between the working electrode 5 and the detecting electrode 7. A current generated between the working electrode 5 and the detecting electrode 7 is converted to a voltage by the current/voltage conversion circuit 118a, and the voltage is converted to a pulse by the A/D conversion circuit 119a to be outputted to the CPU 120.

Next, when a specimen is supplied to the inlet 9a of the specimen supply path of the biosensor A, the specimen is drawn into the specimen supply path, passes on through the counter electrode 6 and the working electrode 5, and reaches the detecting electrode 7. At this point of time, the reagent layer 12 is dissolved, an oxidation-reduction reaction occurs, and electrical changes occur between the working electrode 5 and the detecting electrode 7. The CPU 120 starts the quantification operation, when detecting that the electrical changes have occurred between the working electrode 5 and the detecting electrode 7, that is, a measurable amount of specimen has been supplied to the specimen supply path of the biosensor A, according to changes in the pulse inputted from the A/D conversion circuit 119a.

The CPU 120 turns on the switch 116a to connect the counter electrode 6 to the ground, and controls the current/voltage conversion circuit 118a not to supply the voltage for a prescribed period of time thereafter, so that the reaction between the reagent layer 12 formed on the electrode parts and the specimen is promoted. After the passage of the prescribed period of time, the prescribed voltage is applied between the working electrode 5 and the counter electrode 6 as well as the detecting electrode 7 for about five seconds by the current/voltage conversion circuit 118a.

At this point of time, a current proportional to the concentration of a substrate in the specimen is generated between the working electrode 5 and the counter electrode 6 as well as the detecting electrode 7. The current is converted to a voltage by the current/voltage conversion circuit 118a, and the voltage value is converted to a pulse by the A/D conversion circuit 119a to be outputted to the CPU 120. The CPU 120 counts the number of pulses to calculate a response value, and the result is displayed on the LCD 121.

Figure 14:
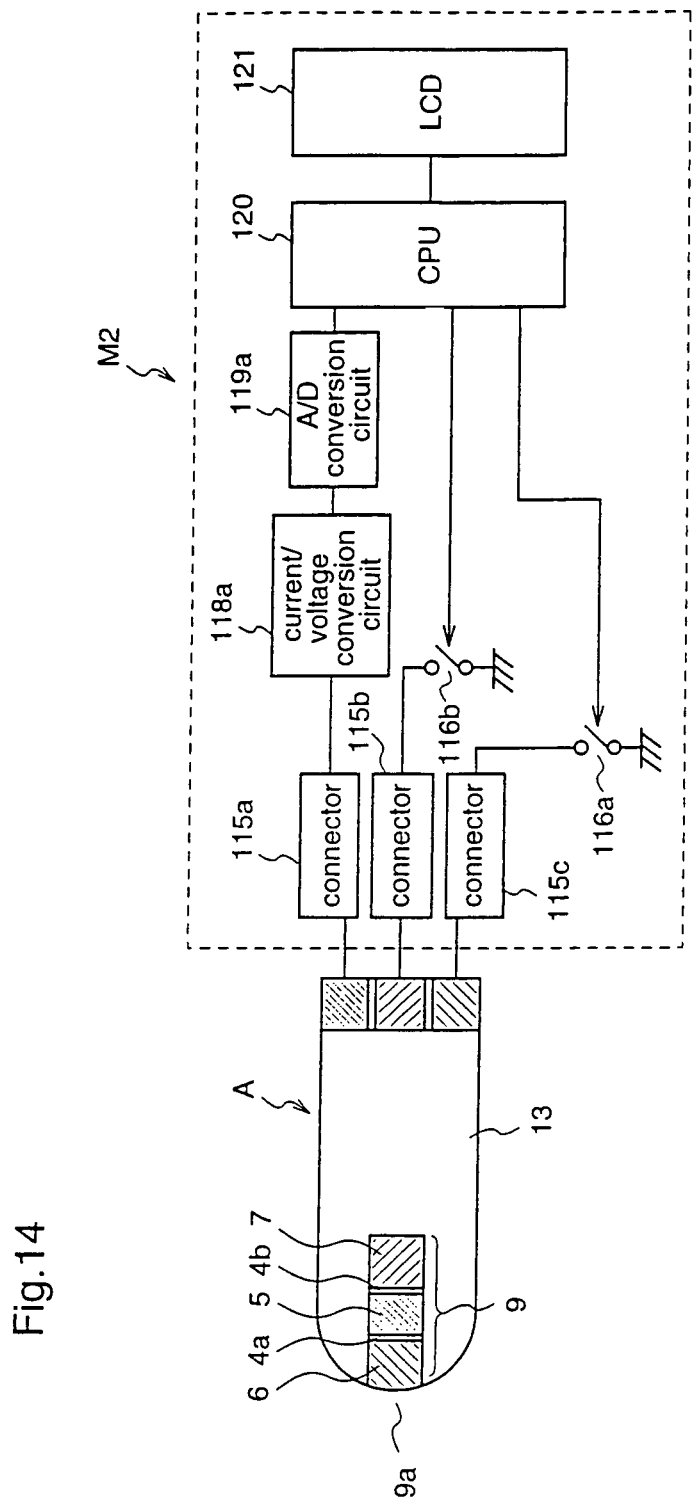
FIG. 14 is a diagram illustrating another structures of the biosensor and the quantification apparatus according to the sixth embodiment.

While the detecting electrode 6 is always connected to the ground here, a quantification apparatus M2 is also possible, which is provided with a switch 116b between the detecting electrode 7 and the ground, and controls ON/OFF of the connection between the detecting electrode 7 and the ground, as shown in FIG. 14. When the biosensor A is connected to the connectors 115a to 115c of the so-constructed quantification apparatus M2, the switch 116a is turned off under the control of the CPU 120, leading to a non-connection state between the counter electrode 6 and the ground, while the switch 116b is turned on, and a prescribed voltage is applied between the working electrode 5 and the detecting electrode 7. Thereafter, the switch 116b remains in the ON-state from the start of the specimen drawing by the biosensor A until the quantification operation of the quantification apparatus M2 is finished, and the quantification operation is the same as that of the above-described quantification apparatus M1.

Then, respective electrode areas of the biosensor preferable for measuring the amount of a substrate included in a sample liquid will be described.

Figure 15:
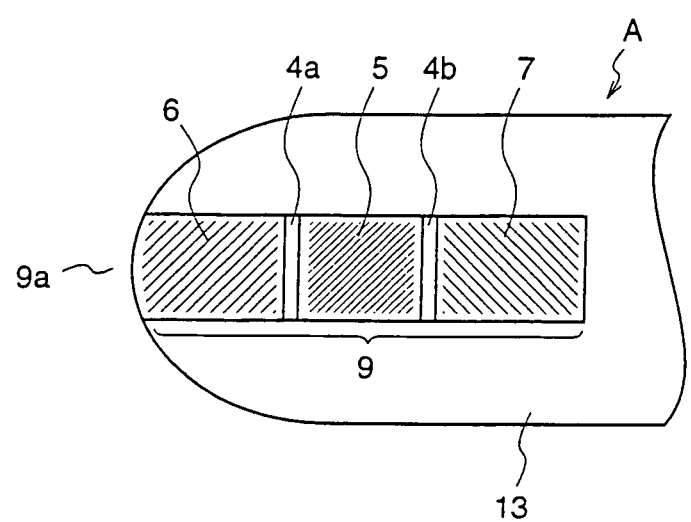
FIG. 15 is an enlarged view of a specimen supply path of the biosensor according to the first embodiment.

FIG. 15 is an enlarged view of the specimen supply path of the biosensor A according to the first embodiment of the present invention. It is generally preferable that the areas of the counter electrode 6, the working electrode 5, and the detecting electrode 7 in the specimen supply path of the biosensor A are such that the area of the counter electrode 6 is equivalent to or larger than that of the working electrode 5 to prevent an electron transfer reaction between the electrodes from being rate-determined.

In the sixth embodiment, the detecting electrode 7 of the biosensor A is also used as a counter electrode at the measuring, and therefore when the total of the areas of the counter electrode 6 and the detecting electrode 7 is equal to or larger than the area of the working electrode 5, an electron transfer reaction between the respective electrodes can be prevented from being rate-determined. For example, when the counter electrode 6 and the working electrode 5 have equivalent areas, and the area of the detecting electrode 7 is set at several-tens percents of the area of the counter electrode 6, the area of the counter electrode 6 and detecting electrode 7 which is equal to or larger than the area of the working electrode 5 can be obtained. Further, in order to perform the electron transfer reaction between the working electrode 5 and the counter electrode 6 as well as the detecting electrode 7 more uniformly, it is desirable that the respective areas of the counter electrode 6 and the detecting electrode 7 adjacent to the working electrode 5 are equivalent as shown in FIG. 15.

As described above, according to the quantification method employing the biosensor A in the sixth embodiment of the present invention, when a specimen is drawn into the specimen supply path of the biosensor A and the electrical changes occur between the detecting electrode 7 and the working electrode 5, the electrical changes are detected and the quantification operation is started in any of the quantification apparatus M1 and the quantification apparatus M2. Therefore, it can be prevented that the quantification apparatus M1 or M2 is inappropriately operated to start the quantification operation regardless of a shortage of the specimen amount supplied to the biosensor A as in the prior art, which results in erroneous operations such as display of erroneous measured values.

Further, in the present invention, when the amount of specimen which can be quantified is supplied to the biosensor A, the detecting electrode 7 is used also as the counter electrode after the start of the quantification, and thus when the total of the areas of the counter electrode 6 and the detecting electrode 7 is at least equivalent to the area of the working electrode 5, the electron transfer reaction between the electrodes is prevented from being rate-determined, thereby to promote the reaction smoothly. At the same time, the capacity of the specimen supply path can be downsized, whereby the quantitative analysis based on a slight amount of specimen, which was conventionally impossible, can be performed properly. Further, when the area of the detecting electrode 7 and that of the counter electrode 6 are equivalent, the electron transfer reaction between the electrodes is performed uniformly, thereby obtaining a more satisfactory response.

Embodiment 7

Hereinafter, a quantification method for quantifying a substrate and a quantification apparatus for quantifying a substrate, which employ any of the biosensors A to D whose electrical conductive layers are formed by employing the thin film electrode forming method described in the fifth embodiment but which are different from those of the above-described sixth embodiment will be described. A biosensor which is employed in a following description is supposed to be the biosensor A described in the first embodiment.

Figure 16:
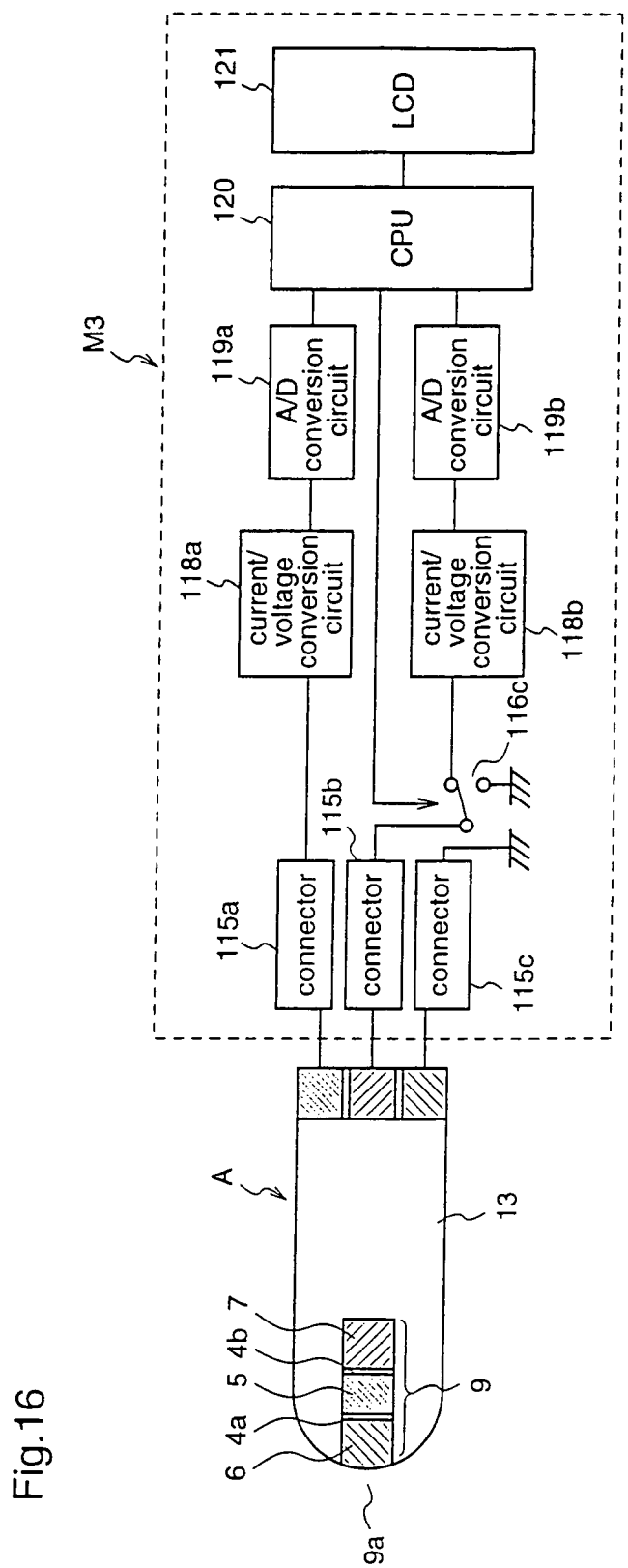
FIG. 16 is a diagram illustrating structures of a biosensor and a quantification apparatus according to a seventh embodiment.

FIG. 16 is a diagram illustrating structures of the biosensor A and a quantification apparatus employed in the quantification method employing the biosensor according to the seventh embodiment of the present invention. In the figure, the same reference numerals as those shown in FIG. 13 denote the same or corresponding parts.

In a quantification apparatus M3, numerals 115a, 115b, and 115c denote connectors connected to the working electrode 5, the detecting electrode 7, and the counter electrode 6 of the biosensor A, respectively, numeral 116c denotes a selector switch which is connected to the connector 115b at one end and is capable of switching the connection between a current/voltage conversion circuit 118b in a latter stage and the ground at the other end, numeral 118a denotes a current/voltage conversion circuit which is connected to the connector 115a and converts a current flowing between the working electrode 6 and other electrode into a voltage to be output, numeral 118b denotes a current/voltage conversion circuit which is connected to the connector 115b via the selector switch 116c and converts a current flowing between the detecting electrode 7 and other electrode into a voltage to be output, numerals 119a and 119b denote A/D conversion circuits which are connected to the current/voltage conversion circuits 118a and 118b, respectively, and convert the voltage values from the current/voltage conversion circuits 118a and 118b into pulses, numeral 120 denotes a CPU which controls the selector switch 116c and calculates the amounts of substrate included in the specimen based on the pulses from the A/D conversion circuits 119a and 119b, and numeral 121 denotes a LCD (liquid crystal display) which displays a measured value calculated by the CPU 120.

Hereinafter, a description will be given of the operations of the biosensor A and the quantification apparatus M3 according to the seventh embodiment of the present invention when the amount of substrate included in a specimen is measured by the quantification method employing the biosensor A.

First, when the biosensor A is connected to the connectors 115a-115c of the quantification apparatus M3, the selector switch 116c is connected to the current/voltage conversion circuit 118b under the control of the CPU 120, and a prescribed voltage is applied between the counter electrode 6 and the working electrode 5 as well as between the counter electrode 6 and the detecting electrode 7. The currents generated between the counter electrode 6 and the working electrode 5 as well as between the counter electrode 6 and the detecting electrode 7 are converted to voltages by the current/voltage conversion circuits 118a and 118b, respectively, and are further converted to pulses by the A/D conversion circuits 119a and 119b.

Next, when the specimen is supplied to the inlet 9a of the specimen supply path of the biosensor A, the specimen is drawn into the specimen supply path, passes through on the counter electrode 6 and the working electrode 5, and reaches the detecting electrode 7. At this point of time, the reagent layer 12 is dissolved by the specimen and an oxidation-reduction reaction occurs, and electrical changes occur between the counter electrode 6 and the working electrode 5 as well as between the counter electrode 6 and the detecting electrode 7.

The CPU 120 detects that the electrical changes have occurred between the counter electrode 6 and the working electrode 5 as well as between the counter electrode 6 and the detecting electrode 7 from the pulses inputted from the A/D conversion circuits 119a and 119b, and confirms that the amount of specimen which can be quantified has been supplied to the specimen supply path of the biosensor A.

Then, the CPU 120 makes the selector switch 116c to be connected to the ground, and controls the current/voltage conversion circuit 118a not to supply the voltage for a prescribed period of time, so that a reaction between the reagent layer 12 formed on the respective electrodes and the specimen is promoted.

After the passage of the prescribed period of time, the prescribed voltage is applied between the working electrode 5 and the counter electrode 6 as well as the detecting electrode 7 for about five seconds by the current/voltage conversion circuit 118a, the CPU 120 calculates a response value based on its current, and the result is displayed on the LCD 121.

However, in a case where the current is generated between the counter electrode 6 and the working electrode 5 by the supply of the specimen to the specimen supply path but no current is thereafter generated between the counter electrode 6 and the detecting electrode 7 for the prescribed period of time, the CPU 120 judges that there is a shortage of the specimen amount, and this is displayed on the LCD 121. Even when the specimen is supplemented to the specimen supply path after the LCD 121 once displays that there is a shortage of the specimen supply, the CPU 120 does not start the quantification operation.

As described above, according to the quantification method employing the biosensor in the seventh embodiment of the present invention, when the specimen is drawn into the specimen supply path of the biosensor A, and electrical changes occur between the counter electrode 6 and the working electrode 5 while no electrical change occurs between the counter electrode 6 and the detecting electrode 7, the quantification apparatus M3 displays on the LCD 121 that there is a shortage of the specimen supply and informs a user of the fact, thereby enhancing the convenience and safety at the measuring.

Embodiment 8

Hereinafter, a quantification method for quantifying a substrate and a quantification apparatus for quantifying a substrate, which employ any of the biosensors A to D whose electrical conductive layers are formed by employing the thin film electrode forming method described in the fifth embodiment but are different from those of the above-described sixth and seventh embodiments will be described. The biosensor employed in a following description is supposed to be the biosensor A described in the first embodiment.

Figure 17:
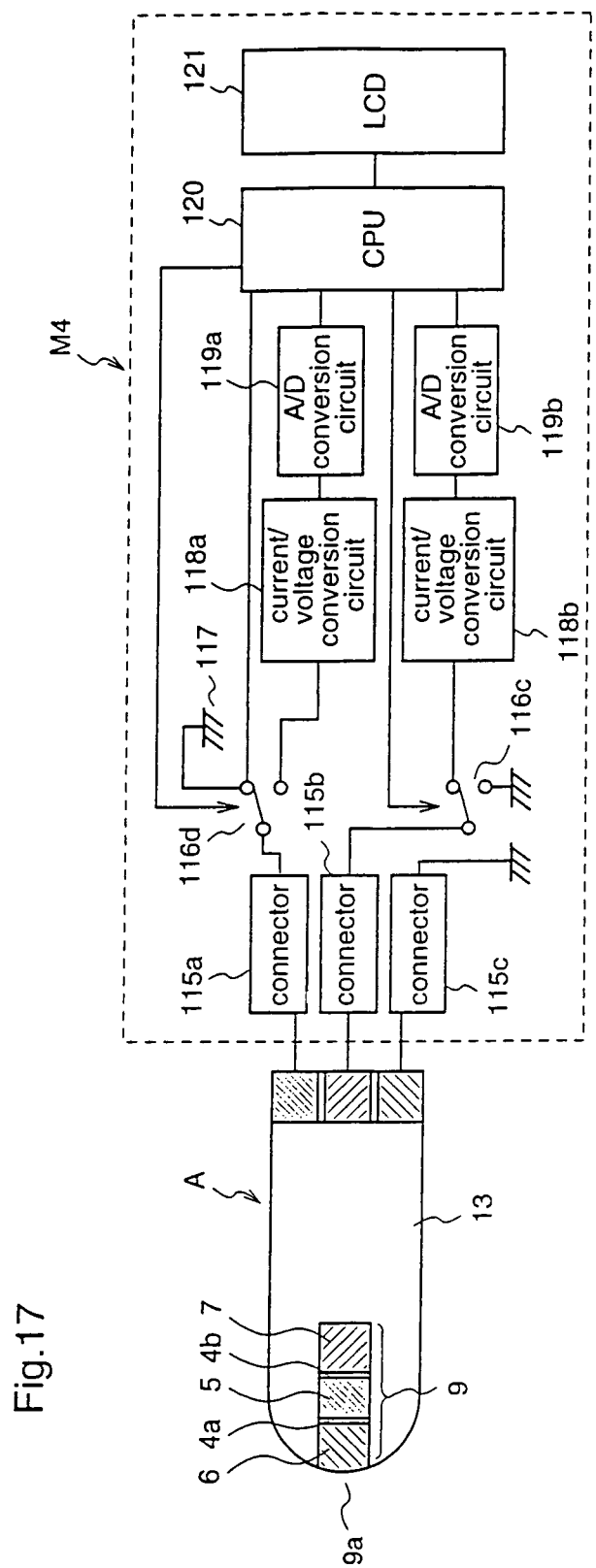
FIG. 17 is a diagram illustrating structures of a biosensor and a quantification apparatus according to an eighth embodiment.

FIG. 17 is a diagram illustrating structures of the biosensor A and a quantification apparatus employed in the quantification method employing the biosensor according to the eighth embodiment of the present invention. In the figure, the same reference numerals as those shown in FIG. 16 denote the same or corresponding parts.

The structure of the quantification apparatus M4 in the eighth embodiment is basically the same as that in the seventh embodiment, while the structure is such that a selector switch 116d is added between the connector 115a and the current/voltage conversion circuit 118a of the quantification apparatus M4 and the connection of the working electrode 5 can be switched between the current/voltage conversion circuit 118a and the ground.

Hereinafter, the operations of the biosensor and the quantification apparatus when the amount of substrate included in a specimen is quantified by the quantification method employing the biosensor according to the eighth embodiment of the present invention will be described with reference to FIG. 17.

First, when the biosensor A is connected to the connectors 115a-115c of the quantification apparatus M4, the selector switches 116d and 116c are connected to the current/voltage conversion circuits 118a and 118b under control of the CPU 120, respectively, and a prescribed voltage is applied between the counter electrode 6 and the working electrode 5 as well as between the working electrode 5 and the detecting electrode 7. Currents generated between the counter electrode 6 and the working electrode 5 as well as between the working electrode 5 and the detecting electrode 7 are converted to voltages by the current/voltage conversion circuits 118a and 118b, respectively, and are further converted to pulses by the A/D conversion circuits 119a and 119b.

Next, the specimen is supplied to the inlet 9a of the specimen supply path of the biosensor A and drawn into the specimen supply path, and when it covers the working electrode 5, electrical changes occur between the counter electrode 6 and the working electrode 5. The CPU 120 detects the electrical changes from the pulse inputted from the A/D conversion circuit 119a, and connects the selector switch 116d to the ground.

When the specimen reaches the detecting electrode 7, electrical changes occur between the working electrode 5 and the detecting electrode 7. The CPU 120 detects the electrical changes from the pulse inputted from the A/D conversion circuit 119b, and confirms that the specimen is sufficiently supplied to the specimen supply path.

Then, the CPU 120 makes the selector switch 116d to be connected to the current/voltage conversion circuit 118a as well as the selector switch 116c to be connected to the ground, to control the current/voltage conversion circuit 118a not to supply the voltage for the prescribed period of time, so that a reaction between the reagent layer 12 formed on the respective electrodes and the specimen is promoted.

After the passage of the prescribed period of time, the prescribed voltage is applied between the working electrode 5 and the counter electrode 6 as well as the detecting electrode 7 for about five seconds by the current/voltage conversion circuit 118a, and the CPU 120 calculates the amount of substrate included in the specimen based on its current, and its measured value is displayed on the LCD 121.

However, in a case where the current is generated between the counter electrode 6 and the working electrode 5 by the supply of the specimen to the specimen supply path but no current is generated between the working electrode 5 and the detecting electrode 7 for the prescribed period of time thereafter, the CPU 120 judges that there is a shortage of the specimen amount, and this is displayed on the LCD 121. Even when the specimen is supplemented to the specimen supply path after the LCD 121 once displays that there is a shortage of the specimen supply, the CPU 120 does not start the quantification operation.

As described above, according to the quantification method employing the biosensor of the eighth embodiment of the present invention, when the specimen is drawn into the specimen supply path of the biosensor A, and electrical changes occur between the counter electrode 6 and the working electrode 5 while no electrical change occurs between the working electrode 5 and the detecting electrode 7, the quantification apparatus M4 displays on the LCD 121 that there is a shortage of the specimen supply and informs a user of the fact, thereby enhancing the convenience and safety at the measuring.

While the biosensor is described as an enzyme sensor in the above-described sixth to eighth embodiments, a biosensor which employs a reagent such as an antibody, a microorganism, a DNA, and a RNA in addition to the enzyme can also be the similar one.

APPLICABILITY IN INDUSTRY

As described above, the biosensor according to the present invention can be formed by a simple manufacturing method, as well as a biosensor which is excellent in a measuring accuracy, a biosensor in which a reagent layer is placed uniformly on electrodes regardless of a reagent liquid composition, resulting in an uniform performance, a biosensor which can keep the performance constant without affecting an area of an electrode when the support is cut, and a biosensor which enables a discrimination of correction data for each production lot only by being inserted without a correction chip inserted can be obtained, and further the thin film electrode forming method according to the invention is suitable for forming an electrical conductive layer of the biosensor, and further the method and the apparatus for quantification according to the invention are quite useful for diagnostics a slight amount of specimen.

The invention claimed is:

1. A method of quantifying substrate content comprising:
    a first detecting step for detecting an electrical change generated between a measuring electrode and a counter electrode of a biosensor by applying a sample liquid to the biosensor;
    a second detecting step for detecting an electrical change generated between a detecting electrode of the biosensor and the counter electrode or the measuring electrode by applying the sample liquid to the biosensor; and
    a notification step for informing a user when the second detecting step does not occur within a predetermined period after the first detecting step.

2. The method of claim 1, where the biosensor comprises:
    a first insulating support;
    a second insulating support;
    a supply path for introducing the sample liquid to the electrodes; and
    a reagent layer for quantifying a substrate included in the sample liquid;
    wherein the electrodes, the supply path, and the reagent layer are situated between the first insulating support and the second insulating support,
    the supply path being provided on the electrodes, and
    the electrodes being formed from an electrically conductive layer that is formed on all or part of an internal surface of one or both of the first insulating support and the second insulating support.

3. A quantifying device providing the quantifying method in claim 2, which comprises:
    a first current/voltage conversion circuit for converting an electric current from the measuring electrode to a voltage;
    a second current/voltage conversion circuit for converting an electric current from the detecting electrode to a voltage;
    a first analog/digital (A/D) conversion circuit for converting the voltage from the first current/voltage conversion circuit; and
    a second A/D conversion circuit for converting the voltage from the second current/voltage conversion circuit;
    wherein the sample liquid is supplied to the reagent layer in the supply path, an electric change is generated between the measuring electrode and the counter electrode, and a means is provided for informing the user that no change is generated when a control part detects that an electric change is not generated between the detecting electrode and the measuring electrode or the counter electrode.

4. The quantifying device as defined in claim 3, which comprises:
    a first switch for switching the connection of the detecting electrode to the first current/voltage conversion circuit or to ground (GND), and
    a control part controlling the first A/D conversion circuit, the second A/D conversion circuit, and the first switch.

5. The quantifying device as defined in claim 4, which comprises:
    a second switch for switching the connection of the measuring electrode to the second current/voltage conversion circuit or to GND, and
    a control part controlling the first A/D conversion circuit, the second A/D conversion circuit, the first switch, and the second switch.

* * * * *